United States Patent [19]
Zezulka et al.

[11] Patent Number: 5,341,854
[45] Date of Patent: Aug. 30, 1994

[54] ROBOTIC DRUG DISPENSING SYSTEM

[75] Inventors: Bohuslav J. Zezulka, Kelowna; Henry H. Voss, North Vancouver; Anne M. Fincati, Calgary, all of Canada

[73] Assignee: Alberta Research Council, Alberta, Canada

[21] Appl. No.: 761,869

[22] PCT Filed: Feb. 27, 1990

[86] PCT No.: PCT/CA90/00066

§ 371 Date: Oct. 16, 1991

§ 102(e) Date: Oct. 16, 1991

[87] PCT Pub. No.: WO90/09776

PCT Pub. Date: Sep. 7, 1990

[30] Foreign Application Priority Data

Sep. 28, 1989 [CA] Canada .................. 613.929

[51] Int. Cl.$^5$ .................. A61J 1/00; B01F 13/00
[52] U.S. Cl. .................. 141/1; 141/2; 141/9; 141/10; 141/18; 141/67; 141/98; 141/100; 141/114; 141/329; 141/129; 141/89; 221/79; 221/225; 414/225; 901/6; 901/7; 156/DIG. 18; 156/DIG. 37; 604/408; 604/414; 604/416
[58] Field of Search .................. 141/1, 2, 9, 10, 18, 141/21-25, 67, 68, 85, 89-92, 98, 100, 104, 250, 311 R, 114, 129, 130, 329, 330; 414/225, 226; 901/6, 7; 366/110, 111, 114; 604/408, 414, 416; 156/DIG. 18, DIG. 37; 422/63-67; 221/79, 88, 232, 171, 200, 225, 236, 239, 278; 198/465.1, 465.3, 465.4, 728, 733, 803.1, 803.01, 803.21

[56] References Cited

U.S. PATENT DOCUMENTS

| | | | |
|---|---|---|---|
| 4,131,426 | 12/1978 | Range | 141/1 |
| 4,307,059 | 12/1981 | Cambio . | |
| 4,417,607 | 11/1983 | Scholle et al. | 141/1 |
| 4,458,733 | 7/1984 | Lyons | 141/1 |
| 4,687,403 | 8/1987 | Motoda | 414/225 |
| 4,807,676 | 2/1989 | Cerny et al. | 141/98 |
| 4,842,028 | 6/1989 | Kaufman et al. | 141/114 |
| 5,122,342 | 6/1992 | McCulluch et al. | 422/65 |
| 5,203,385 | 4/1993 | Waber | 366/111 X |

FOREIGN PATENT DOCUMENTS 3518476 11/1986 Fed. Rep. of Germany ........ 221/79
8807710 10/1988 PCT Int'l Appl. .

OTHER PUBLICATIONS

Py Technology, Zymark Corporation, Sep. 1986, pp. 1-11 and 22.
Zymate Laboratory Automation System, Zymark Corporation, Sep. 1986, entire document.

Primary Examiner—J. Casimer Jacyna
Attorney, Agent, or Firm—Beveridge, DeGrandi, Weilacher & Young

[57] ABSTRACT

The invention concerns the automated robotic system for dispensing drugs from vials into liquid containers such as IV bags or syringes. A robot selects a vial and a suitable container and transports them to a processing station together with a needle which may be double-ended. At the processing station the contents of the vial are transferred into the container. Some of the contents of the container may be transferred into the vial in order to reconstitute and/or wash out the vial contents and agitation may be provided for the vial. Various additional devices may be provided such as a decapping device for the vials, an alcohol swabbing station for swabbing the top of a vial and/or the input port of a IV bag or syringe. Moreover, a label printer may be provided so that the robot may deliver a label with the finally processed IV bag and empty vial to a verification station. When IV bags are used, the invention may feature a conveyor of trays of the bags to a pick-up station of the robot. The trays add rigidity to the bags so that they can be handled by the robot. To present needles to the robot, needle trays may be used in which needles lie in parallel one to the other in pick-up position. The robot may have gripping fingers having one gripping surface for gripping a vial and another gripping surface for gripping a needle or solution container. The containers may be provided with shaped portions for gripping by either of the robot gripping surfaces. Vial dispensers may be a chute or a series of chutes which present vials to specific pick-up locations from which the robot can select a vial in accordance with prescription data.

41 Claims, 28 Drawing Sheets

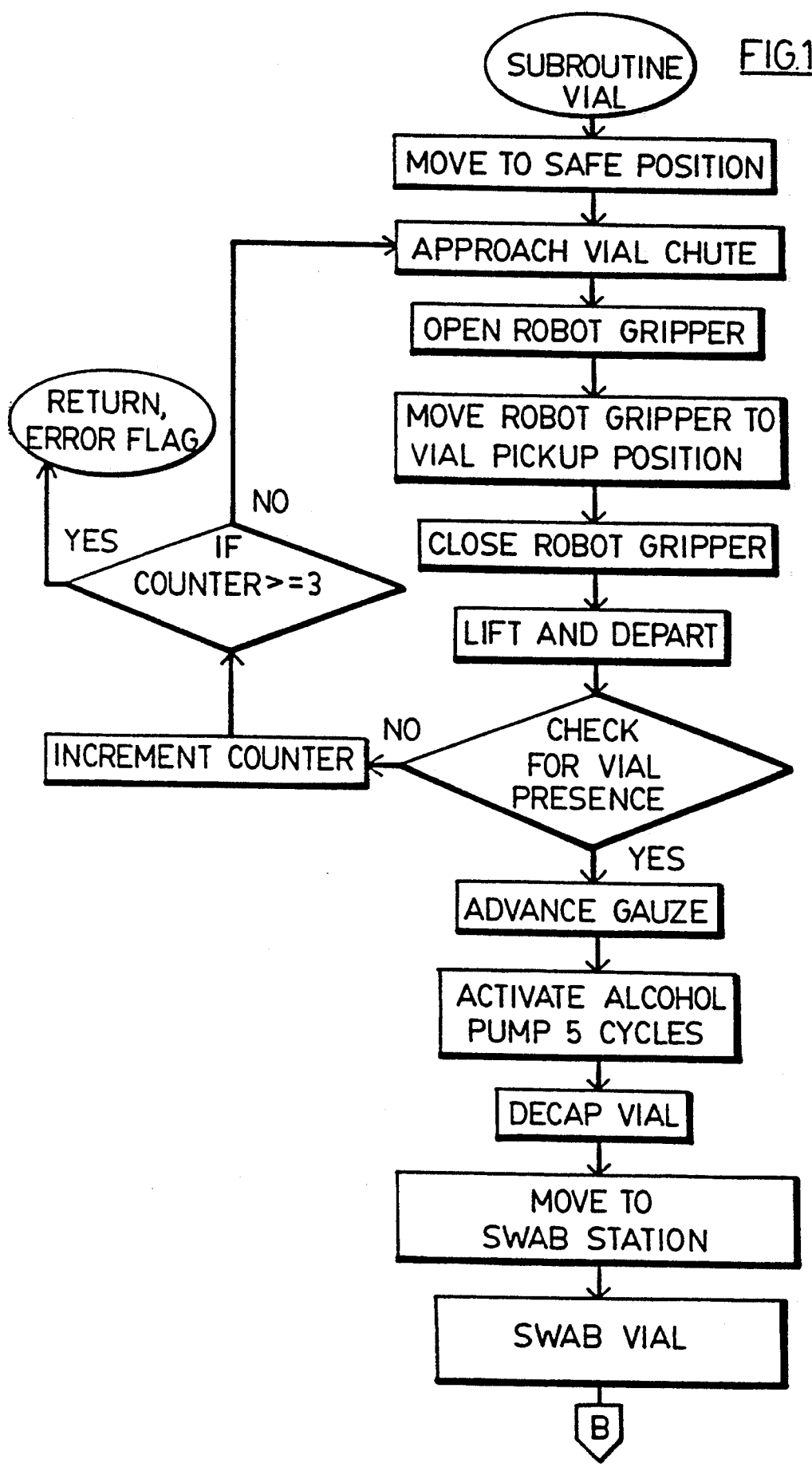

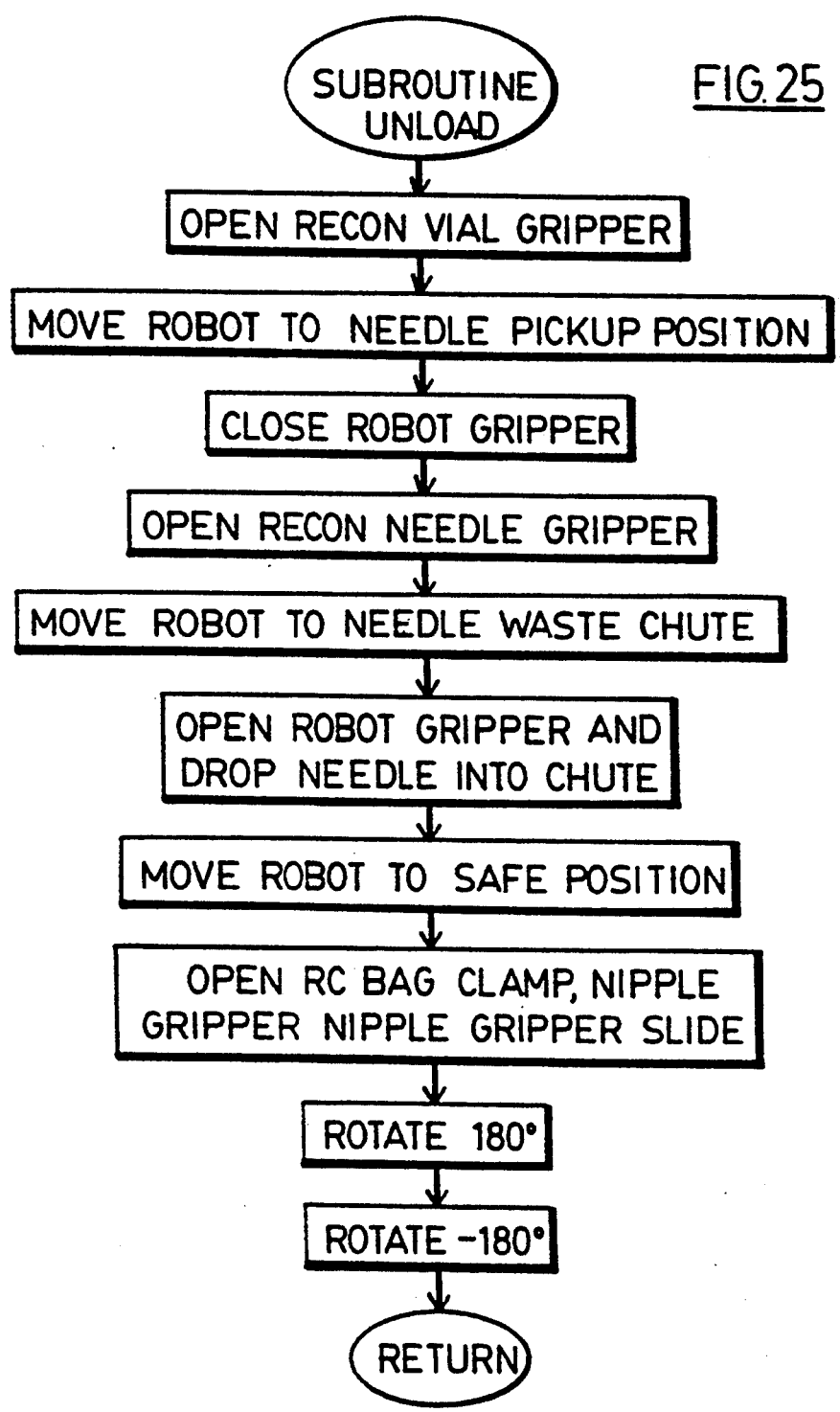

ROBOTIC DRUG DISPENSING SYSTEM

TECHNICAL FIELD

The invention relates to an automated robotic dispensing system for combining a unit drug dose from a vial with a solute for the drug in an IV bag or syringe.

BACKGROUND ART

Generally the task of reconstituting antibiotic or other pharmaceuticals as well as performing fluid transfers from unit drug dose vials is carried out manually. Such work may be performed in a variety of environments such as in a pharmacy or by nursing staff in hospital. Whatever the environment the manual work results in a large amount of technician work load. The resulting labour cost has contributed to the expense of health care.

Typically, in the current procedure, a prescription is received by the pharmacy admixture area. While practice may vary, a pharmacist or other technician may gather all required components, verifying they have not exceeded their shelf life and are the correct constituents, and places them in any tray or container along with the original prescription, in a container which may be a tray made of for example stainless steel or plastic. This tray is placed within a laminar filtered air flow hood. A technician then performs the reconstitution procedure and places the IV bag, the empty drug vial and the original prescription back into the tray. The tray is then checked by another technician where the prescription is again verified against the solute and the empty drug vial and inventory records are updated.

Moreover, the use of sterile conditions when mixing drug doses into solution in IV bags is of prime importance. The fact that the prescription will enter a patient's circulatory system means that any risk of contamination must be eliminated. Such conditions are difficult to achieve and dictate procedures which lengthen the preparation time, increasing unit production cost.

DISCLOSURE OF THE INVENTION

The invention aims to provide an automated robotic system whereby technician time may be reduced thereby increasing productivity, and in which sterile conditions may be maintained. Moreover, it is also an aim to provide a system in which errors or inconsistencies of technique may be reduced or eliminated.

Accordingly the invention provides an automated robotic dispensing system for introducing a unit drug dose from a vial having a top diaphragm pierceable by a needle into a container of solute therefor, comprising a filling station including a manipulating robot, a vial dispenser, a container dispenser for said containers, a needle dispenser, a processing unit and a loading location of an output means for processed containers; the robot being programmed to receive a said vial containing a said unit drug dose from a vial pick-up location of the vial dispenser and deliver it to a vial reception location of the processing unit; receive a said container from the container dispenser at a container pick-up location and deliver the container to a container reception location of the processing unit; receive a said needle from the needle dispenser at a needle pick-up location and deliver the needle to a needle holder of the processing unit; receive the processed container from the processing unit and deliver it to the output; and receive the empty vial from the processing unit and deliver it to the output; receive the used needle from the processing unit and discard it to a discard location; the vial dispenser being adapted to hold a plurality of vials each containing a said unit drug dose and to deliver them sequentially to the vial pick-up location; the container dispenser being adapted to hold a plurality of containers containing solute for the drug dose and to deliver them sequentially to the pick-up location; the needle dispenser being adapted to hold a plurality of double ended needles and to deliver them sequentially to the pick-up location; the processing unit including means for moving the vial, the needle and the corresponding container into fluid communication through the needle, and means for flowing fluid from the container to the vial and vice-versa to dissolve the drug dose and transfer the solution to the container.

The containers may be IV bags or syringes or, indeed any other container. Usually, however, it is an IV bag or a syringe which is to be used for directly introducing a drug into the patient by means of a needle. The IV bags are commonly either of 50 ml or 100 ml but other sizes are possible.

Most commonly the integers of the filling station will be enclosed in a filtered environment so that filling of the containers may be carried out under conditions as sterile as possible. One such suitable environment is an enclosure having a filter hood.

The output may be any convenient means having a loading location at the filling station and a delivery location remote from it. For example, the output may be a chute extending out of the filling station or it may be a carousel extending between the filling station and an area outside it.

The top diaphragm of the vial is usually initially covered with a cap which may be a flip top cap, possibly formed of metal foil. The robot may take the vial to a decapping station prior to any alcohol swabbing station for removal of the cap to expose the diaphragm.

Thus the system may comprise a robotic filling station comprising three feed devices which supply unit dose drug vials, IV bags or syringes, and double-ended filter needles, and the processing station for forming or reconstituting the drug solution in the bag or syringe. The robot is used as an intelligent transfer mechanism to move the vials, the needles and the IV bags or syringes between stations which perform the required tasks. The robotic area is suitably in a Hepa-filtered enclosure with the filtration unit mounted above. The output carousel removes the reconstituted IV bag and empty drug vial to an operator area for prescription verification. Additional stations may be the alcohol swabbing station to swab the top of the vial, and a label printer.

The operator area may comprise a prescription verification area, a prescription input area, and a loading area and a storage area. Prescription input might be done manually by the technician via a terminal and keyboard connected to the workcell computer or preferably by description ordering connected directly with the main hospital computer system. The manual verification of the prescription will be done at least until such time as the bar code technology is applied to these products.

The drugs are supplied in unit dose drug vials. The vials contain either drug powder which is reconstituted into liquid form, or drug already in liquid form which is introduced into the IV bag or syringe for administration to patients.

The invention also provides a process for introducing, in a filling station, a unit drug dose from a vial having a top diaphragm pierceable by a needle into an IV bag of solute therefor, the filling station comprising a manipulating robot, a vial dispenser, an IV bag dispenser, at least a needle pick-up location of a needle dispenser, a processing unit and a reception location of a conveyor for processed IV bags, the pieces comprising the steps of sequentially delivering a said vial to a pick-up location of the vial dispenser which is adapted to hold a plurality of vials each containing a said unit drug dose; sequentially delivering a said IV bag to a pick-up location of the IV bag dispenser which is adapted to hold a plurality of IV bags containing solute for the drug doses; and sequentially delivering in similar orientation a said needle to the pick-up location of the needle dispenser which is adapted to hold a plurality of double ended hollow needles. The process further includes the robot receiving a said vial containing a said unit drug dose from the vial pick-up location of the vial dispenser and delivering it to a vial reception location of the processing unit; the robot receiving a said IV bag from the IV bag dispenser at the IV bag pick-up location and delivering the bag to a bag reception location of the processing unit; the robot receiving a said needle from the needle dispenser at the needle pick-up location and delivering the needle to a needle holder of the processing unit; at the processing unit, moving the vial, the needle and the corresponding IV bag into fluid communication through the needle, and flowing fluid from the IV bag to the vial and vice-versa to dissolve the drug dose and transfer the solution to the IV bag; the robot receiving the processed IV bag from the processing unit and delivering it to the conveyor; the robot receiving an empty vial from the processing unit and delivering it to the conveyor; and the robot receiving the used needle from the processing unit and delivering it to a discarding location.

The vial feeder may present all possible vials to the robot simultaneously. The robot will move to the location of the required vial, as determined by the prescription, and pick it up from the vial dispenser. The robot may then move the vial to a decapping device, and then to an alcohol swab station, when present, where the top of the vial is swabbed. The robot then places the vial at the vial reception location of the processing unit where it is grasped at or near the top. The vial may conveniently be of conventional design being topped by a resilient diaphragm, suitably of rubber, pierceable by a said needle and surrounded by a metal foil collar, suitably of aluminum. Before processing, the collar forming part of a cover for the diaphragm, the central portion of which is the flip top cap, may be presented at the decapping device so that it may be stripped away.

The needle dispenser advances a said needle forward to the pick-up position. Each needle is a conventional double ended needle and may have a long end and short end. Sensors may be provided at this position to determine the orientation of the needle, whether the long end needle is to the right or left of centre. The robot moves to the needle pick-up position, removes a sheath of the needle and discards it and then grasps the needle and moves it to the needle reception location of the processing unit.

The IV bag or syringe dispenser advances one position, placing a said bag or syringe in the pick-up location. The robot takes the bag or syringe and, if the alcohol swab station is provided, an input port of the bag or syringe is swabbed with a fresh section of alcohol soaked gauze. The robot then moves the bag or syringe to the processing unit where the bag or syringe is loaded. If bags are used, they may be loaded into trays to impart rigidity to them to make handling more convenient. There is no objection to using trays for syringes but generally they may not be necessary.

The processing unit or reconstitution station now has the drug vial, the double ended needle, and the container lined up, one above the other. The drug vial is moved directly upwards such that the needle pierces the diaphragm of the vial. The container is moved down, such that the other end of the needle pierces the input port of the bag. Fluid is forced from the bag into the vial where it mixes with or dissolves the drug. The combination of vial, needle and container may then be inverted to facilitate drawing back of the liquid together with the drug into the container.

During processing, a label printer may generate a label with the specific details of the prescription on it. The robot may place this label in the output for delivery with the respective empty vial and filled container.

After processing is completed, the robot removes the empty drug vial and may place it in an appropriate output to be received in a tray of a carousel outside the filtered environment. The deposit of the used vial and the IV bag in the same tray may provide a check that the appropriate drug dose has been added to the bag. The robot also removes the IV bag and places it on the same tray of the carousel.

It should be noted that the above description of the workcell operation can be streamlined to take advantage of periods of inactivity by the robot. For example, the robot could be removing the drug vial and IV bag, swabbing them, and placing them in a drying station to let the alcohol evaporate while the reconstitution station is active. The order of events may be altered slightly; for example, the needle may be placed into the processing unit first instead of second.

BRIEF DESCRIPTION OF THE DRAWINGS

Embodiments of the invention will now be described by way of example with reference to the drawings in which:

FIG. 19 is a flow chart of sub-routine vial, referred to in FIG. 18;

FIG. 25 is a flow chart of sub-routine unload referred to in FIG. 18.

MODES FOR CARRYING OUT THE INVENTION

Figure 1:
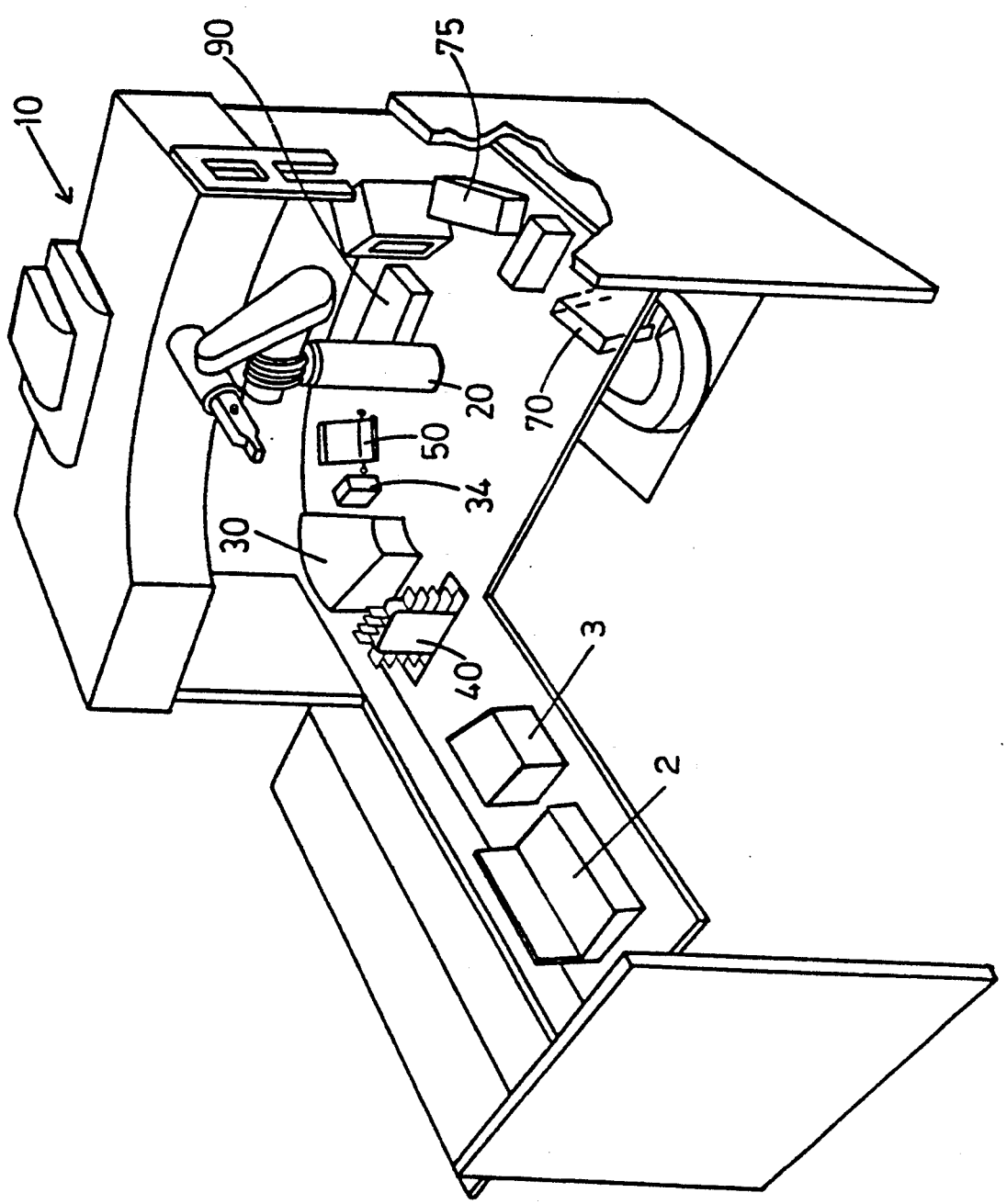
FIG. 1 is a general non-specific view of a work station embodying the present invention.

In the drawings, FIG. 1 shows a general unspecific layout of one embodiment of an automatic dispensing system according to the invention including a sterile enclosure 10, which may be a Hepa filtered enclosure. Inside enclosure 10 are provided a manipulator robot 20, a vial dispenser 30, a decapping device 34, an IV bag dispenser 40, an alcohol swab station 90, a needle dispenser 50, a processing unit 60 (not shown) and part of an output 70 which projects out of the enclosure 10 through an aperture 80 (not shown). Outside the enclosure 10 are the control computer 2 and robot controller 3. For simplicity the enclosure 10 is not shown in the remaining drawings but it is to be understood that it is at least preferably present in all cases.

The control computer 2 and robot controller may be in any convenient location for example in an operator area indicated in FIG. 1.

Figure 2:
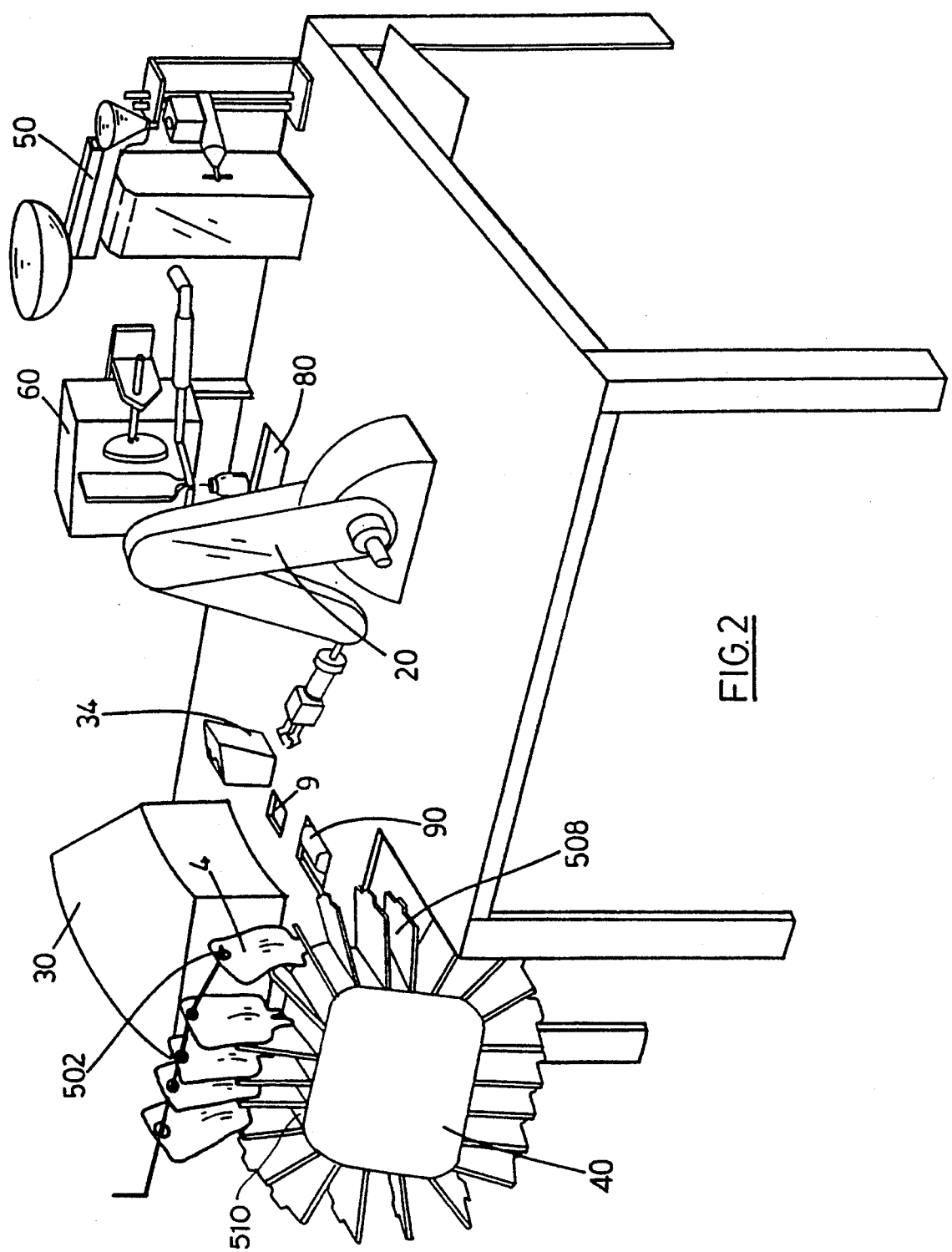
FIG. 2 is a diagrammatic view of a practical work station embodying the invention, the locations of the integers being in working relationship.
Figure 3:
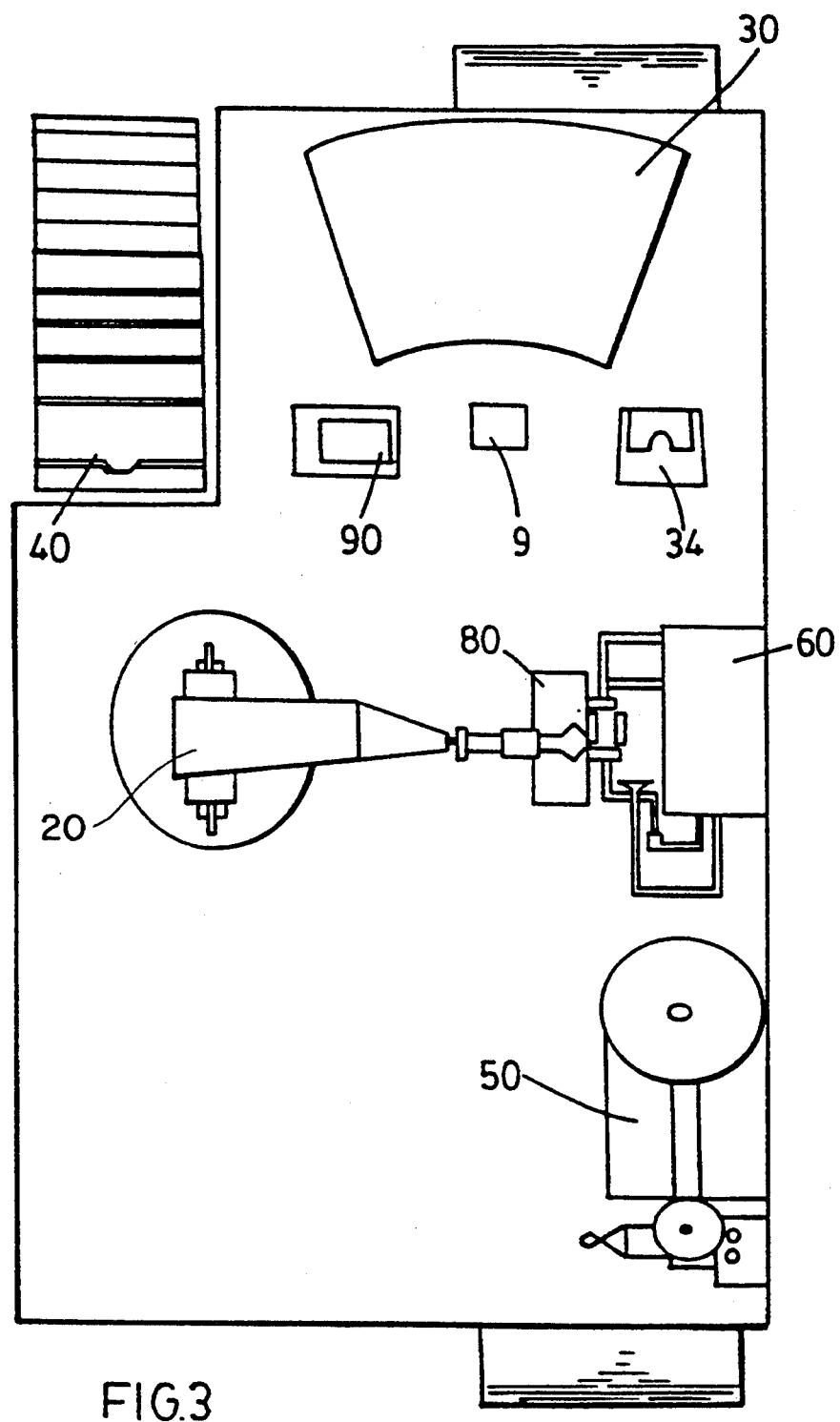
FIG. 3 is a plan of the apparatus of FIG. 2.

FIGS. 2 and 3 show a more specific preferred working layout of a dispensing system according to the invention.

There are several relevant parameters which must be considered when selecting a robot 20. The robot must have the necessary movement capabilities and the accuracy to pick up and place the components in the desired locations; it must have the intelligence to perform many tasks, depending on the prescription to be filled; it should require low maintenance and be inexpensive; and it should be robust.

The small robot market has three categories: the laboratory, the industrial, and the general purpose/research markets. The laboratory robots are typically small general purpose robots with enhanced controllers. The industrial robots have similar payloads as the others but have much higher accuracy and repeatability and lower maintenance requirements. The primary disadvantage of the industrial robots is cost, they are typically twice as expensive as the general purpose robots.

Some available robots are the ERX, Zymark Zymate, Perkin Elmer, Cyber Fluor (CRS Plus), Toshiba SR-606V, Seiko RT2000, Westinghouse Puma 260, Microbot Alpha 11, UMI RTX Personal Robot and the CRS Plus Inc. CRS Robot.

The robot should have gripper means suitable for grasping each of a variety of vials, containers and needles, so that they are presented in the proper orientation for the next operation. Thus the gripper fingers may be such, and the presentation of the vials, containers and needles to the gripper fingers may be such, as to ensure that the center axis of rotation is the same for each object. Thus the position of the top of any vial is known by the computer controller, and the position of the input port of a container or the center section of a needle is also similarly known. Particularly desirable characteristics of the gripper fingers will be discussed in relation to tasks performed.

Figure 17:
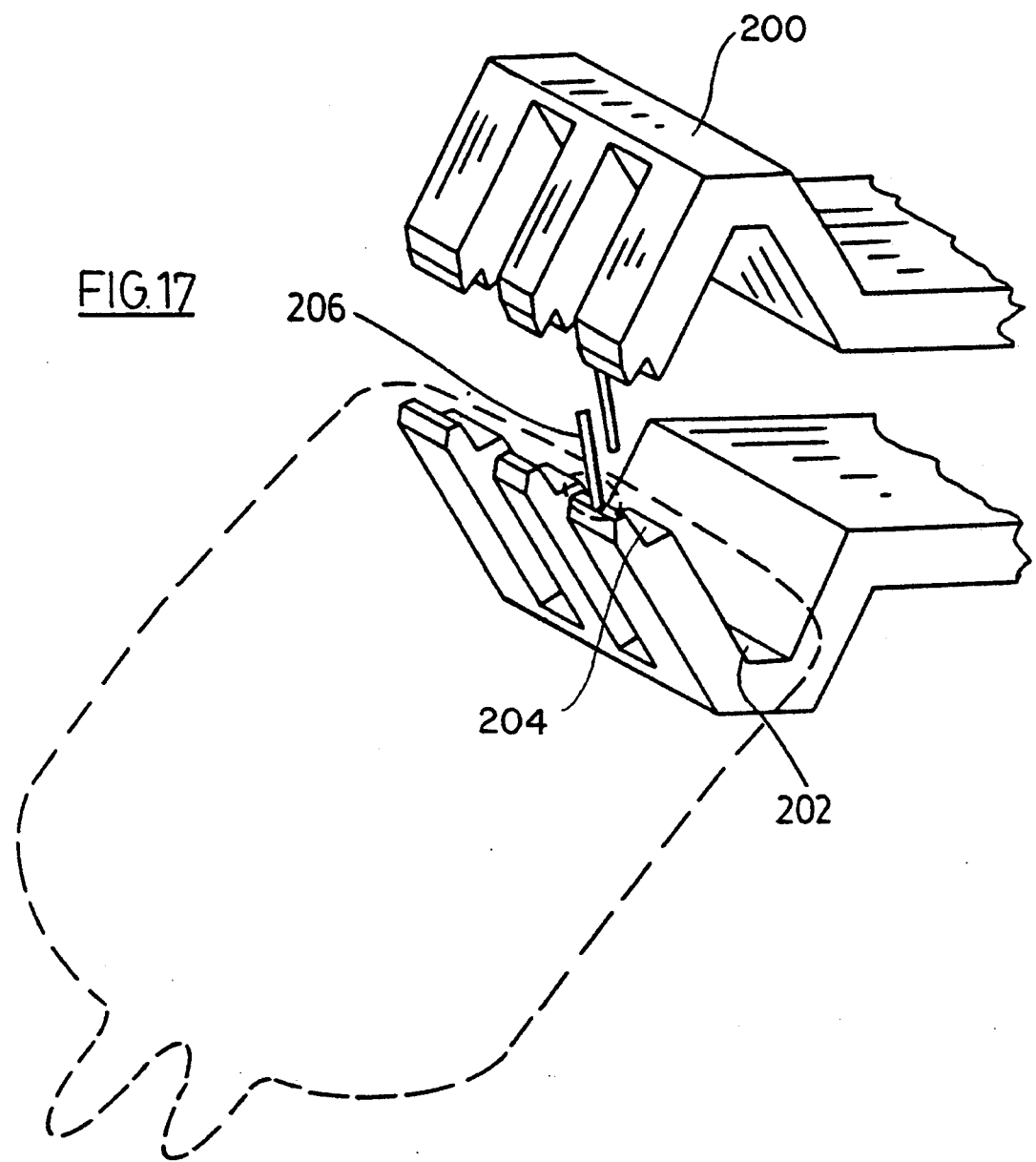
FIG. 17 shows an embodiment of robot gripper fingers.

Additionally the gripper fingers 200 (see FIG. 17) should be such that they may handle vials, containers and needles. The gripper fingers 200 illustrated by way of example have major angled portions 202 suitable for gripping a vial therebetween, and minor angled portions 204 for gripping a needle therebetween. A portion 400 of the IV bag tray 42, shown in FIGS. 6 and 7 may be formed to fit into minor angled portions 204 so the IV bag tray 42 may be handled by gripper fingers 200. The gripper fingers 200 should be provided with electrical sensing means 206 so that the gripper arms may sense when they are correctly located for any task, i.e. gripping air or gripping plastic.

A computer controller may be required by the system to coordinate and control the actions of all the devices as well as provide an interface to the operator. There are many potential dedicated industrial controllers which could meet these requirements but typically these are fairly expensive. The alternative is to use a relatively cheap personal computer such as an IBM PC (or clone) and add interface boards.

Programming for the computer controller is conventional and will present no problems. However by way of example, programming may be in accordance with the following Flow Charts of FIGS. 18-25 which are largely self-explanatory. It will be clear that modifications and changes to the flow sequence may be made and that programming follows from the flow sequences.

The flow charts of FIGS. 18-25 represent simple routines which may be varied by addition or modifications. Features general to the work station operation, or input by an operator may include:

FLOW DESCRIPTION

Queuing of prescriptions according to time or priority.

Checking of operational status of system, e.g.:
all devices are in run mode;
no windows into the environment are open;
time has elapsed to flush "unclean" air from the work environment.

Figure 18:
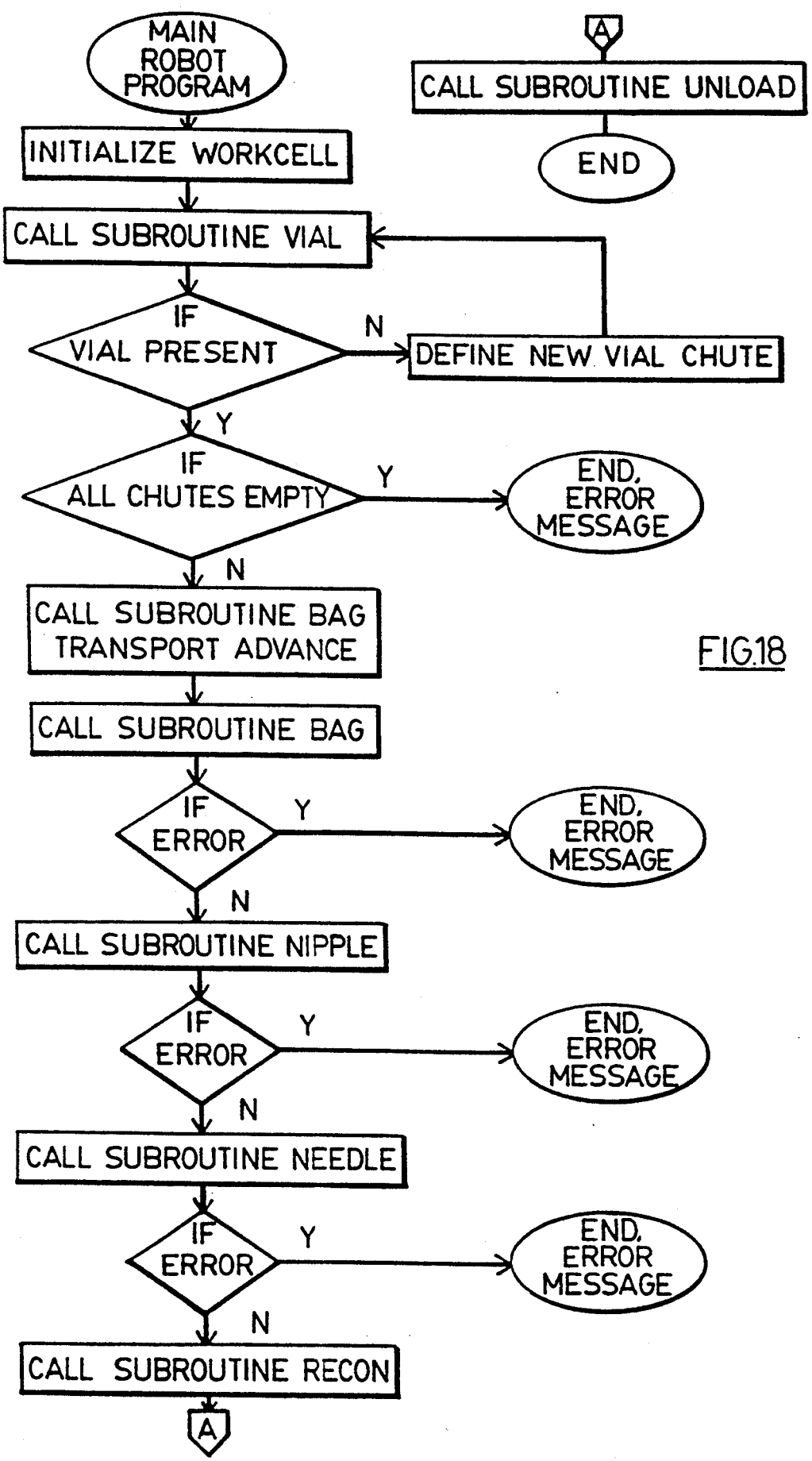
FIG. 18 is a flow chart of the operations for the main routine for the robot.

In the main robot program as shown in FIG. 18, the control computer signals robot controller:
which vial location is to be used;
which IV bag is to be picked up;
what is the length of low-pressure piston time required for fluid transfer to the vial from the IV Minibag;

what is the length of low-pressure piston time required for fluid transfer from the vial to the IV Minibag;

what is the length of time for vial agitation in the process device;

whether or not the prescription is a fluid transfer or a reconstitution.

(Optionally on the capability of the robot controller selected the Control Computer may signal the robot controller with the above information for the next three prescriptions such that the robot can perform movement tasks while the process device is performing the reconstitution and/or the fluid transfer).

Figure 19A:
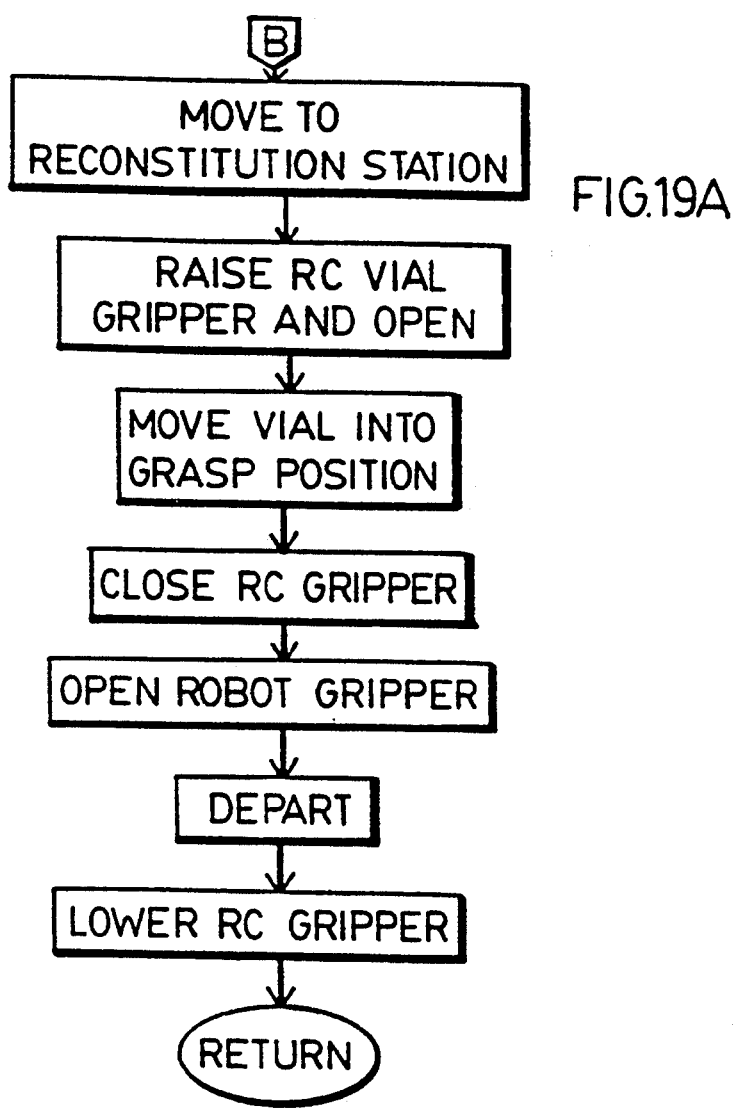
FIG. 19A is a continuation of FIG. 19.

The robot selects and transfers a vial to processing unit, for example according to the flow chart of FIG. 19:

The robot moves to the vial approach frame of the specific vial chute containing the vial identified by the Computer Controller.

The robot moves the gripper fingers to the vial pickup frame.

The robot closes the gripper fingers.

The robot raises the gripper holding the vial.

The robot moves the vial to a depart frame of the vial dispenser chute, avoiding collision with the vial dispenser.

The robot moves the vial to the cap removal station approach frame.

The robot moves the vial to the cap contact frame.

The robot moves the vial along a line perpendicular to the cap removal bracket, forcing the cap to be flipped off. The cap falls into a waste chute.

The vial is moved to a depart frame of the cap removal station.

The vial is moved to the vial approach frame of the alcohol swab station.

The alcohol swab station is signalled to prepare for swabbing. It will inject a small amount of alcohol onto the swab surface.

The vial is moved to contact the swab surface of the alcohol swab station.

The vial is moved back and forth across the swab surface of the alcohol swab station on the alcohol soaked section of gauze.

The vial is moved to a depart position.

The alcohol swab station is signalled by the robot controller that it is clear of the station.

The alcohol swab station advances the gauze to a fresh section.

The vial is moved to the approach frame of the processing unit.

The vial is moved to the vial inset frame of the processing unit.

The processing unit device is signaled and the gripper in the device closes to grasp the top of the vial. The processing unit then signals back to the robot controller that it has gripped the vial.

Figure 20:
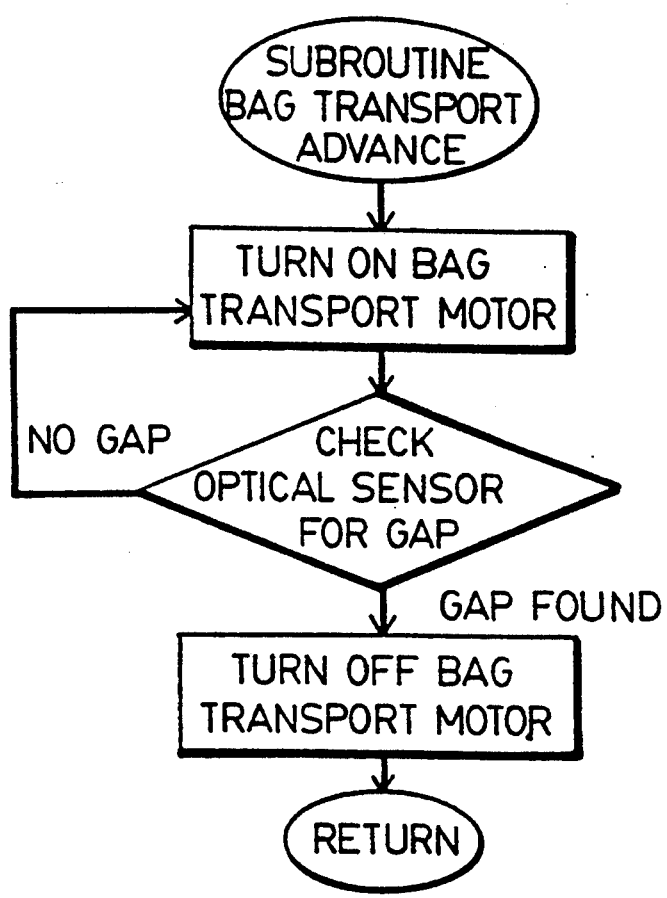
FIG. 20 is a flow chart of the sub-routine bag transport advance, referred to in FIG. 18.

The robot then selects and transfers to the processing unit an IV bag for example according to the flow chart of FIG. 20:

The robot opens the gripper fingers and then moves to the vial depart frame.

The robot moves the gripper fingers to the IV bag dispenser approach frame.

The robot controller signals to the IV bag dispenser which bag type and size it requires (if this option is present). This signal may occur earlier in the program.

The IV bag dispenser advances (or may reverse) to a position where the correct bag is at the pickup location.

The robot moves the gripper fingers to the IV bag pickup frame.

Figure 5:
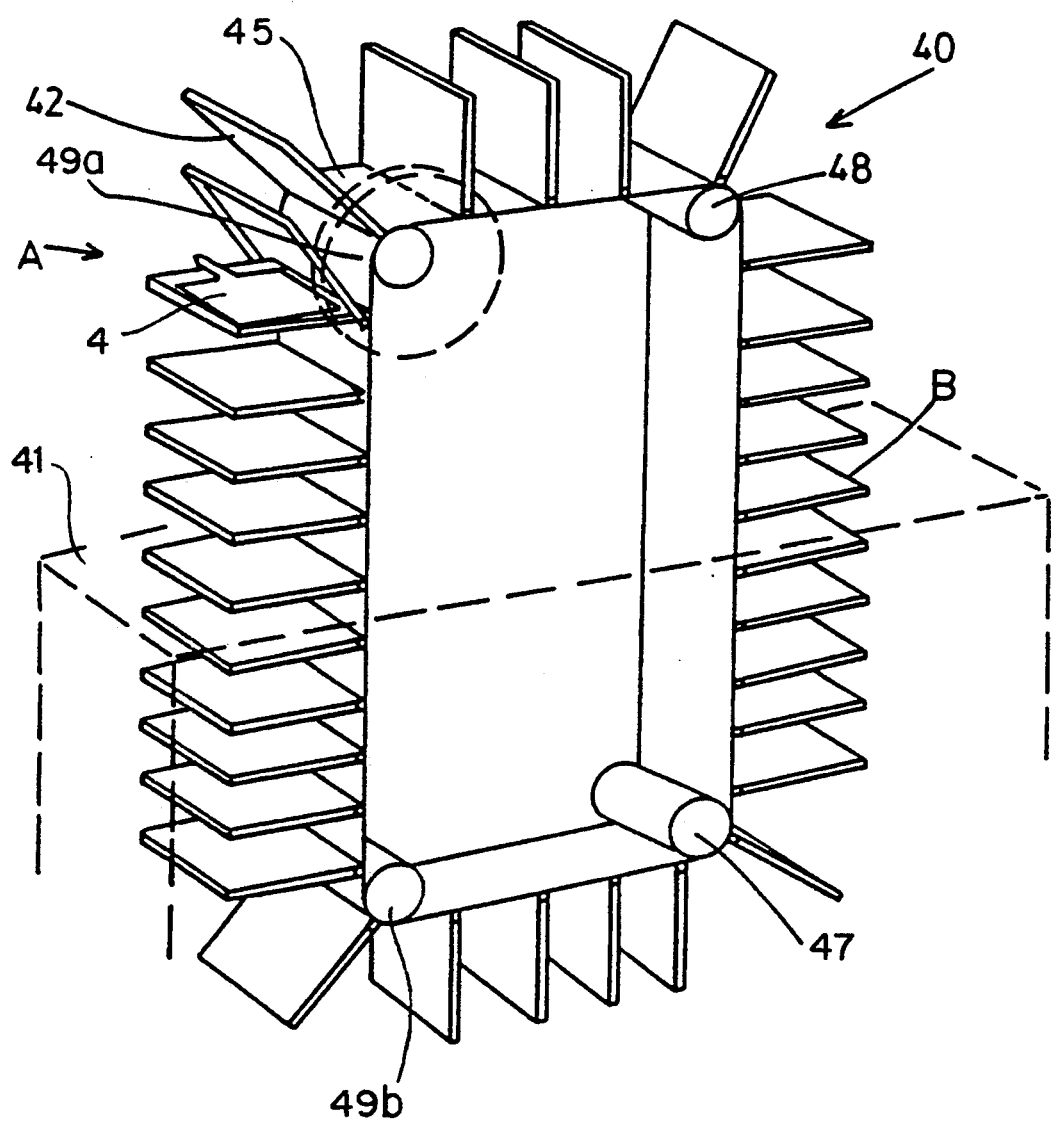
FIG. 5 shows one embodiment of an IV bag feeder.
Figure 6:
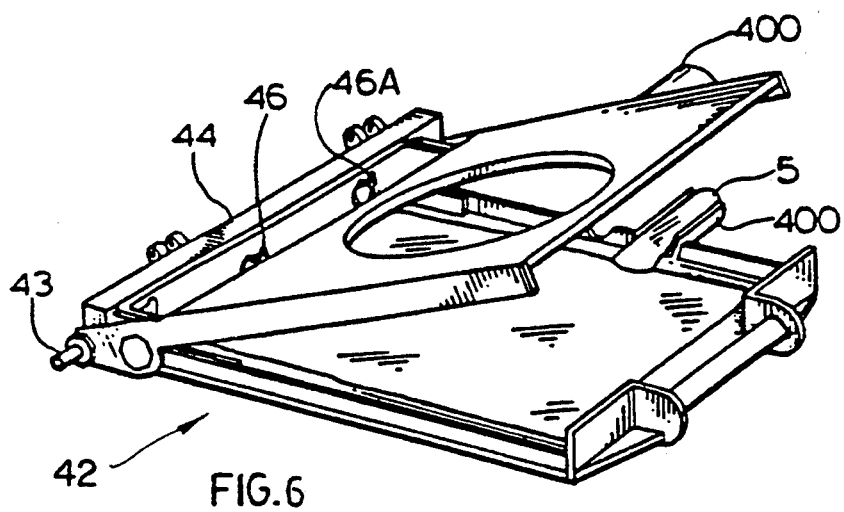
FIG. 6 shows one embodiment of yet an assembled bag tray for the feeder of FIG. 5.
Figure 7:
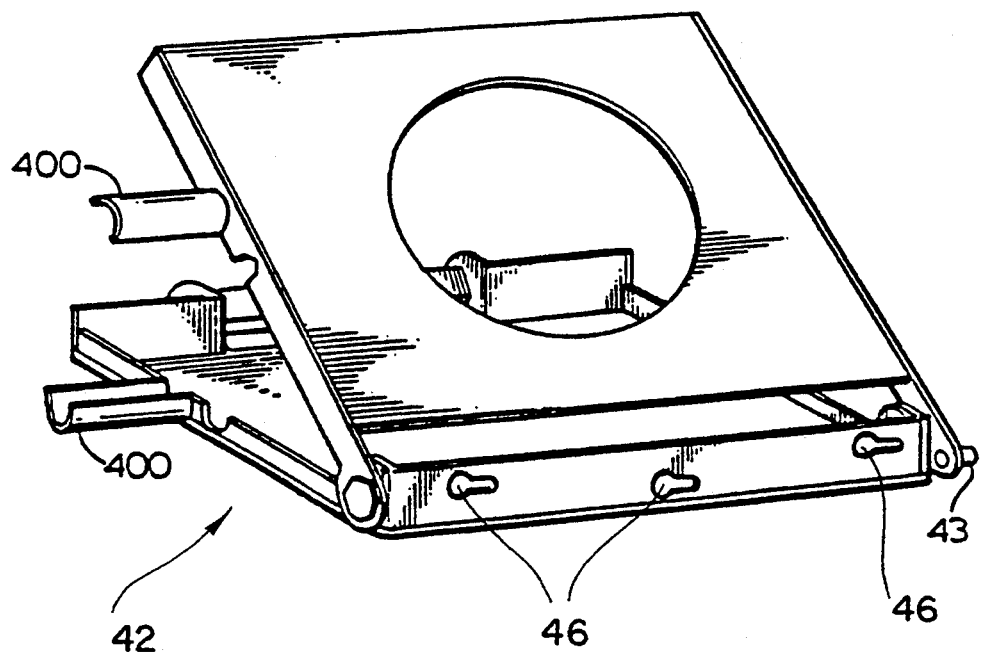
FIG. 7 shows the bag tray of FIG. 6 without the support member.

When the IV bag dispenser is, for example, as illustrated in FIGS. 5, 6 and 7, the sequence of events may be along the following lines:

The gripper fingers are closed.

The robot moves the gripper fingers sideways to unlock the IV bag and tray from the locating keys on the slat holding the tray.

The robot moves the tray to the alcohol swab station tray approach frame.

The alcohol swab station is signalled to prepare for swabbing. It will inject a small amount of alcohol onto the swab surface.

The input port of the bag is moved by the robot such that it comes in contact with the alcohol soaked section of gauze.

The input port of the bag is moved back and forth across the alcohol soaked gauze.

The tray is moved back from the alcohol swab station to the tray depart frame.

The alcohol swab station is signalled to advance the gauze to a fresh section.

The tray is moved to the processing unit tray approach frame.

Figure 13:
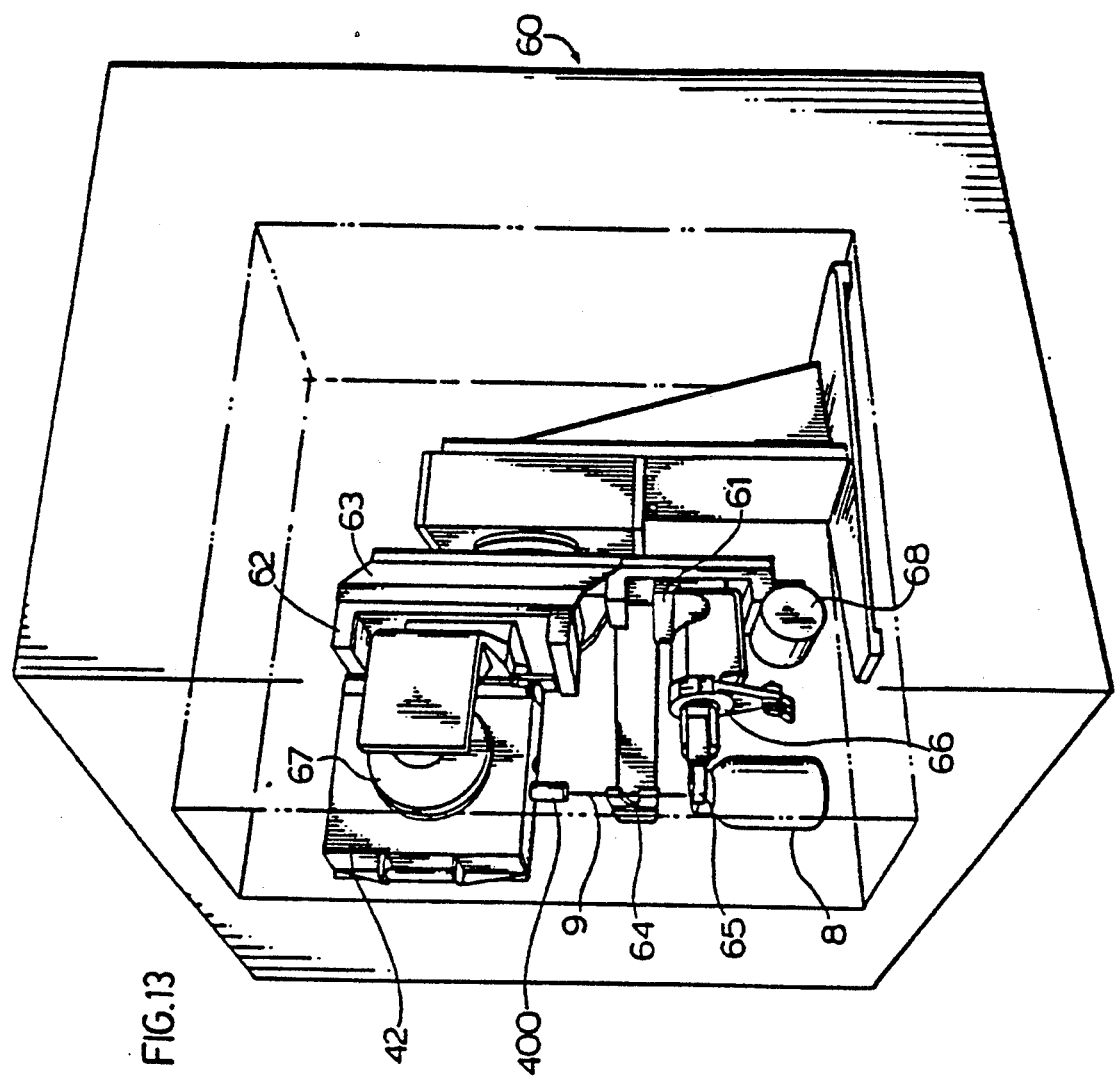
FIG. 13 shows an embodiment of a processing unit which might be used with the bag tray of FIGS. 6 and 7.

The tray is moved to the tray insert frame of the processing unit (see FIG. 13).

The robot controller signals the processing unit that the tray is in the correct tray insert position.

The processing unit activates a solenoid which locks the tray in position on the top pneumatic slide unit of the device.

The robot opens the gripper fingers.

The robot moves the gripper fingers to the tray depart frame.

The processing unit is signalled that the robot is clear.

Figure 8:
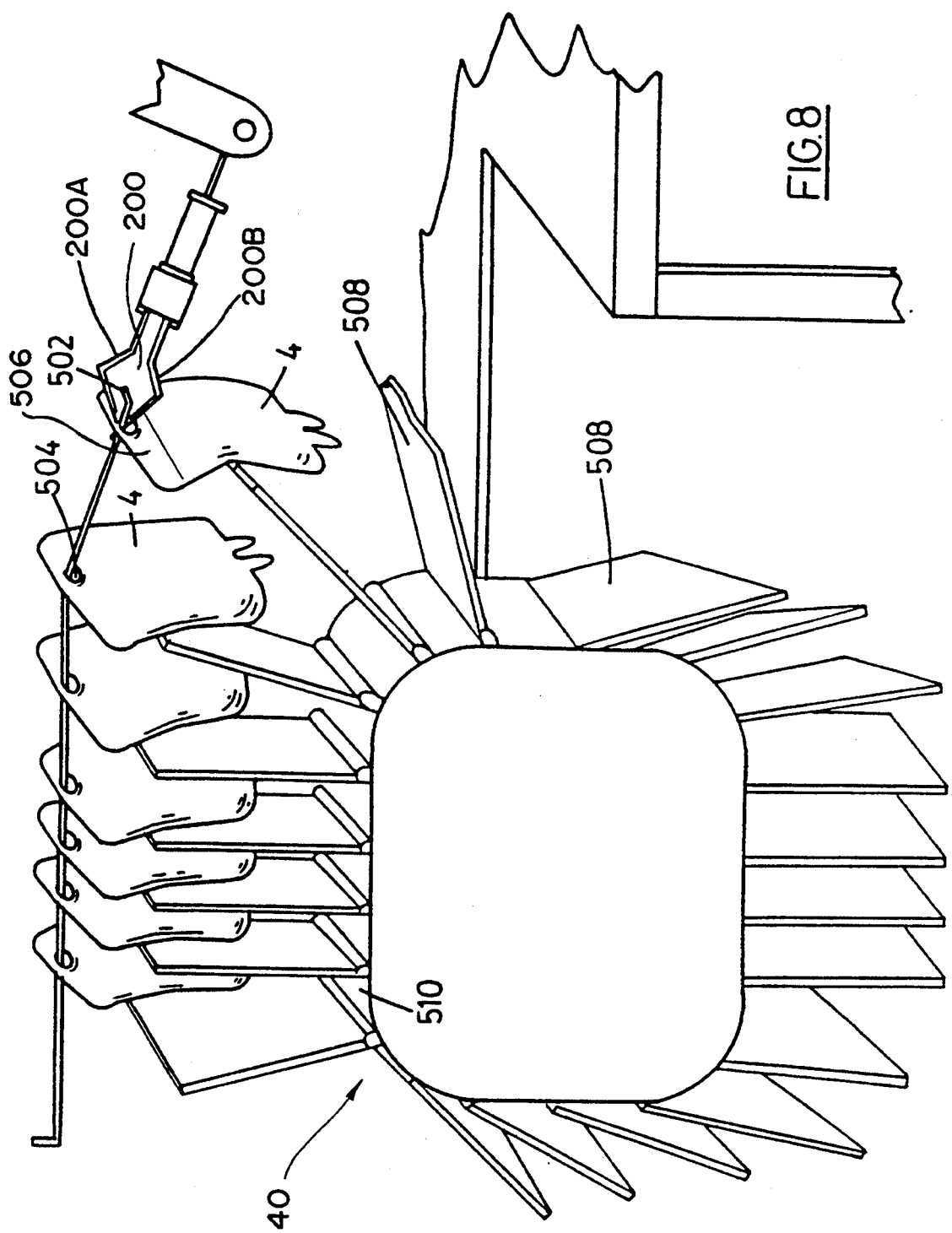
FIG. 8 shows a more preferred IV bag feeder.
Figure 21:
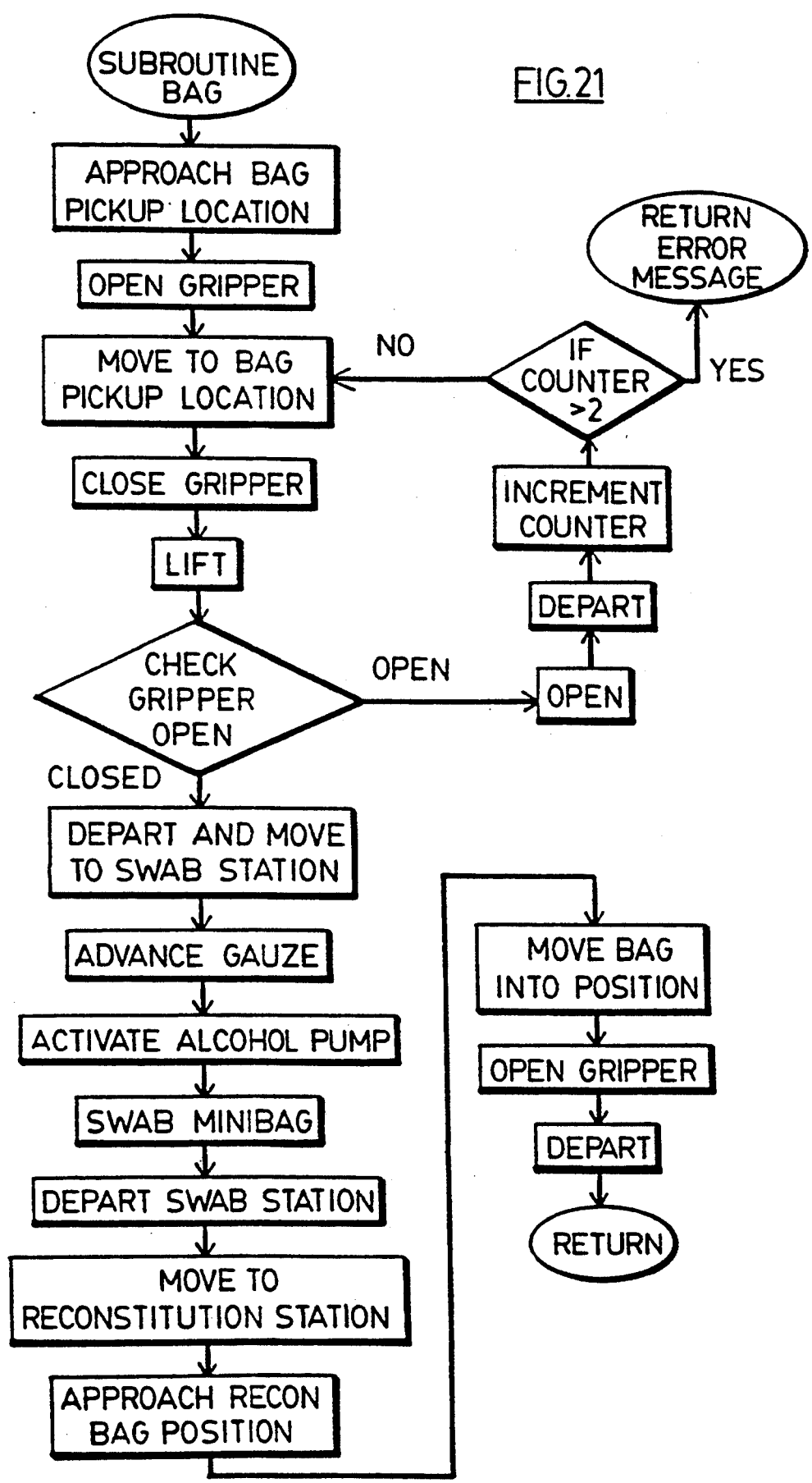
FIG. 21 is a flow chart of the sub-routine bag, referred to in FIG. 18.
Figure 22:
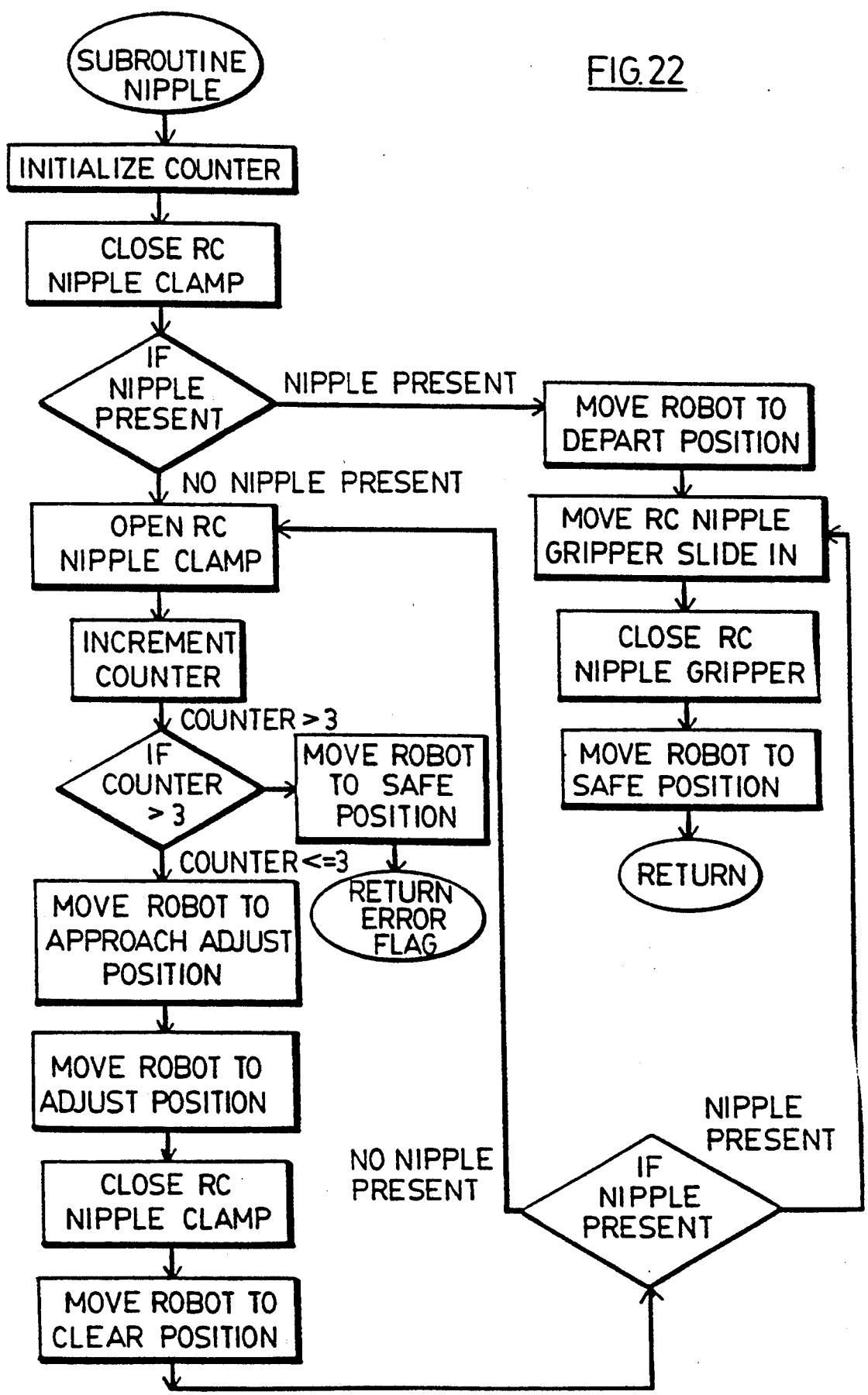
FIG. 22 is a flow chart of sub-routine nipple, referred to in FIG. 18.

When the IV bag feeder is as illustrated in FIG. 8, the routine may be simple following more accurately the flow chart of FIG. 21:

On the arrival of the gripper fingers at the IV bag pick-up, the electrical sensor senses the presence of a hole in a tab of the bag.

The robot moves the gripper hook into the hole and remove the IV bag from the hook of the pickup.

The robot moves the IV bag to the alcohol swab station tray approach frame.

The alcohol swab station is signalled to prepare for swabbing. It will inject a small amount of alcohol onto the swab surface.

The input port of the bag is moved by the robot such that it comes in contact with the alcohol soaked section of gauze.

The input port of the bag is wiped on the alcohol soaked gauze.

The IV bag is moved back from the alcohol swab station.

The alcohol swab station is signalled to advance the gauze to a fresh section.

The IV bag is moved to the processing unit approach frame.

Figure 14:
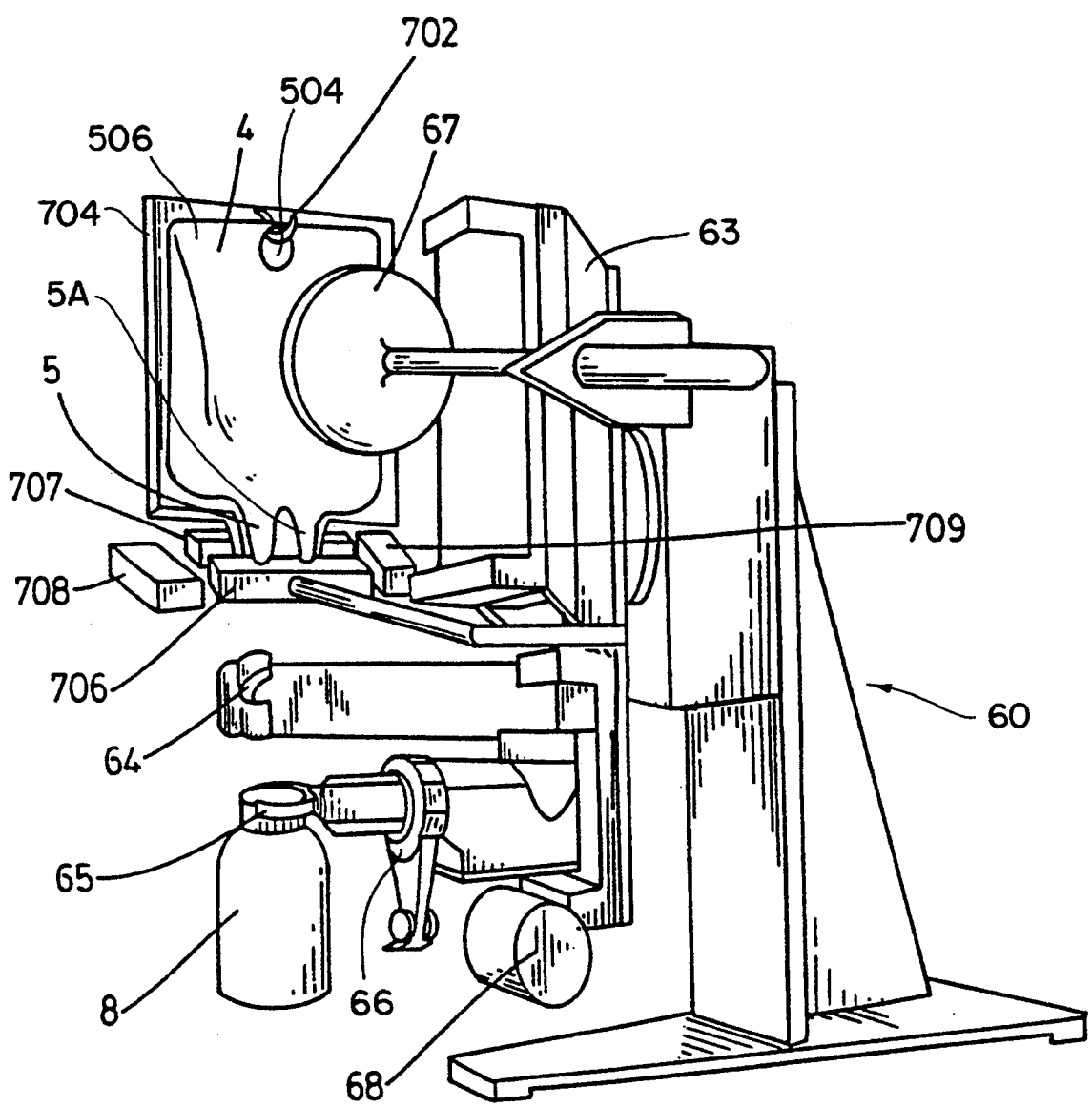
FIG. 14 shows an embodiment of a preferred processing unit able to process IV bags without trays from, for example, a bag feeder such as that of FIG. 8.
Figure 15:
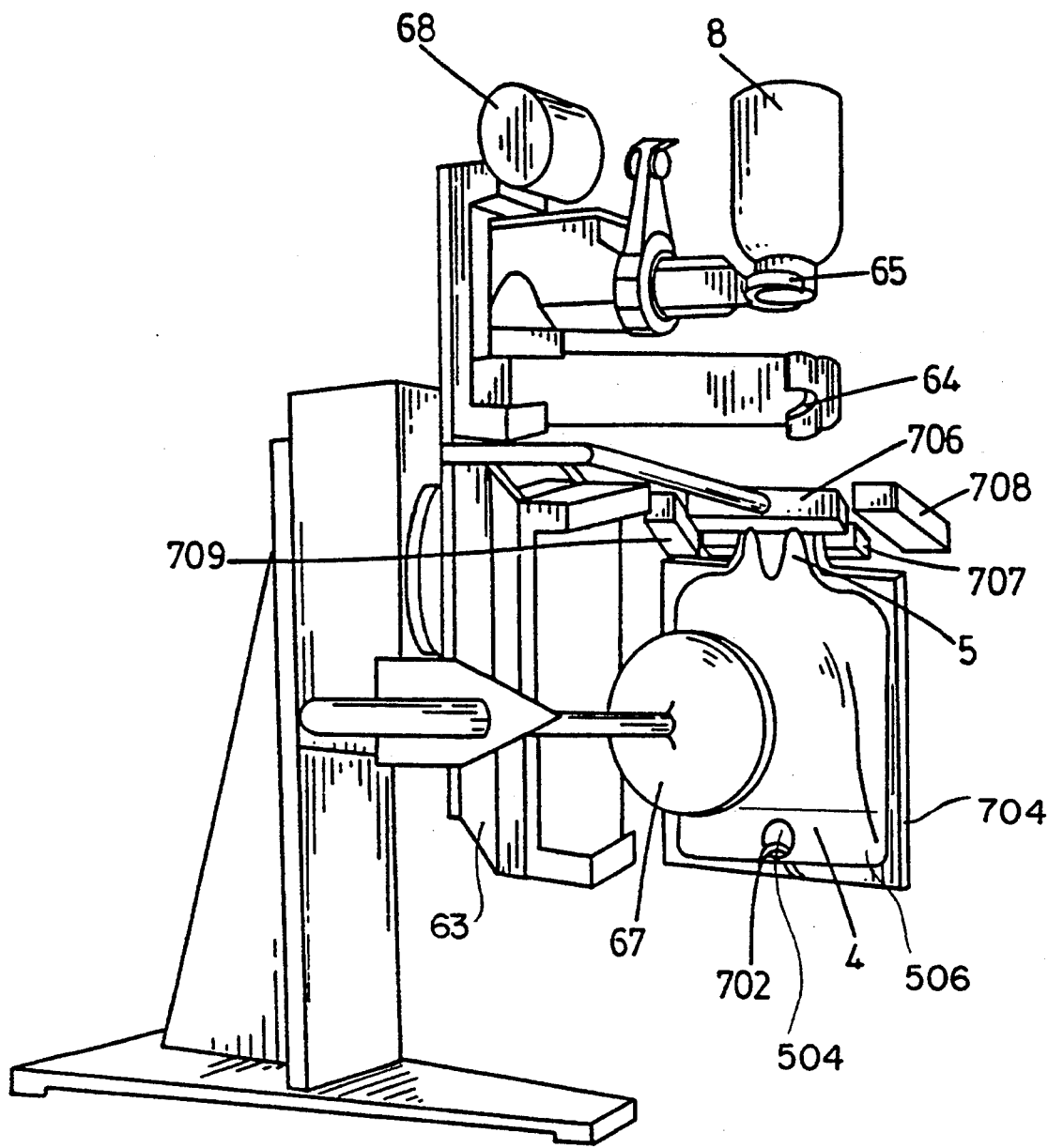
FIG. 15 shows the apparatus of FIG. 14 in inverted position.
Figure 16:
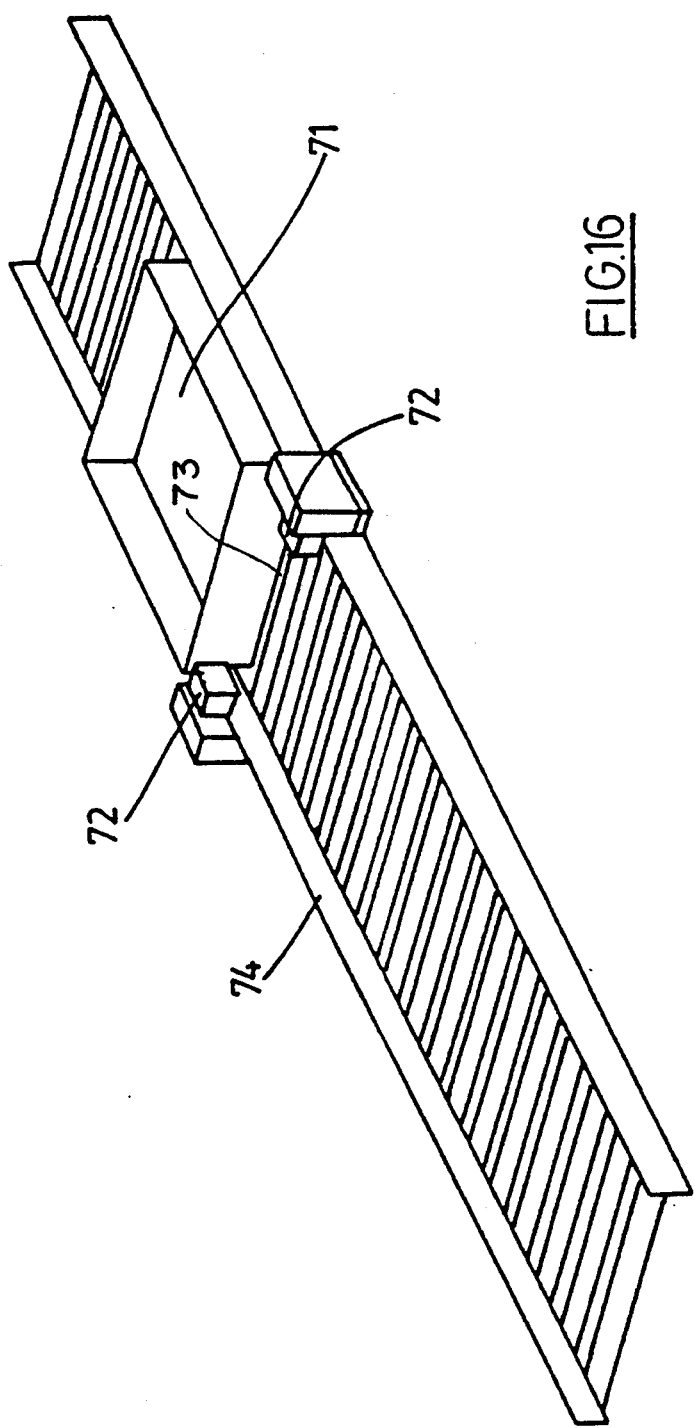
FIG. 16 shows an embodiment of a conveyor which may be used to collect IV bags.

The IV bag is hooked on a hook of the insert frame of the processing unit (see FIGS. 14 and 15).

The robot controller signals the processing unit that the bag is in the correct bag insert position.

The processing unit activates a solenoid which moves locking bars to lock the ports of the bag in position.

The robot then selects and transfers a needle and transports it to the processing device. This may be done either by the routines 1) or 2) outlined below, or by any other convenient routine. Alternative 1) is intended for use with particularly designed needle trays. Alternative 2) is intended for use with loose needles:

1)

The robot moves the gripper fingers to an approach frame of the needle pickup location;

The robot checks to ensure the gripper fingers are open;

The robot moves the gripper fingers to the needle pickup frame.

Note: this needle pickup frame is dependent on the number of needles already picked up from the needle tray.

The gripper fingers are closed.

The robot departs from the needle pickup frame by a small distance.

The robot moves through an unobstructed path to an approach frame of the needle clip of the processing unit.

The robot inserts the needle in the processing unit needle clip.

The gripper fingers are opened.

The robot departs to a set distance.

Figure 23:
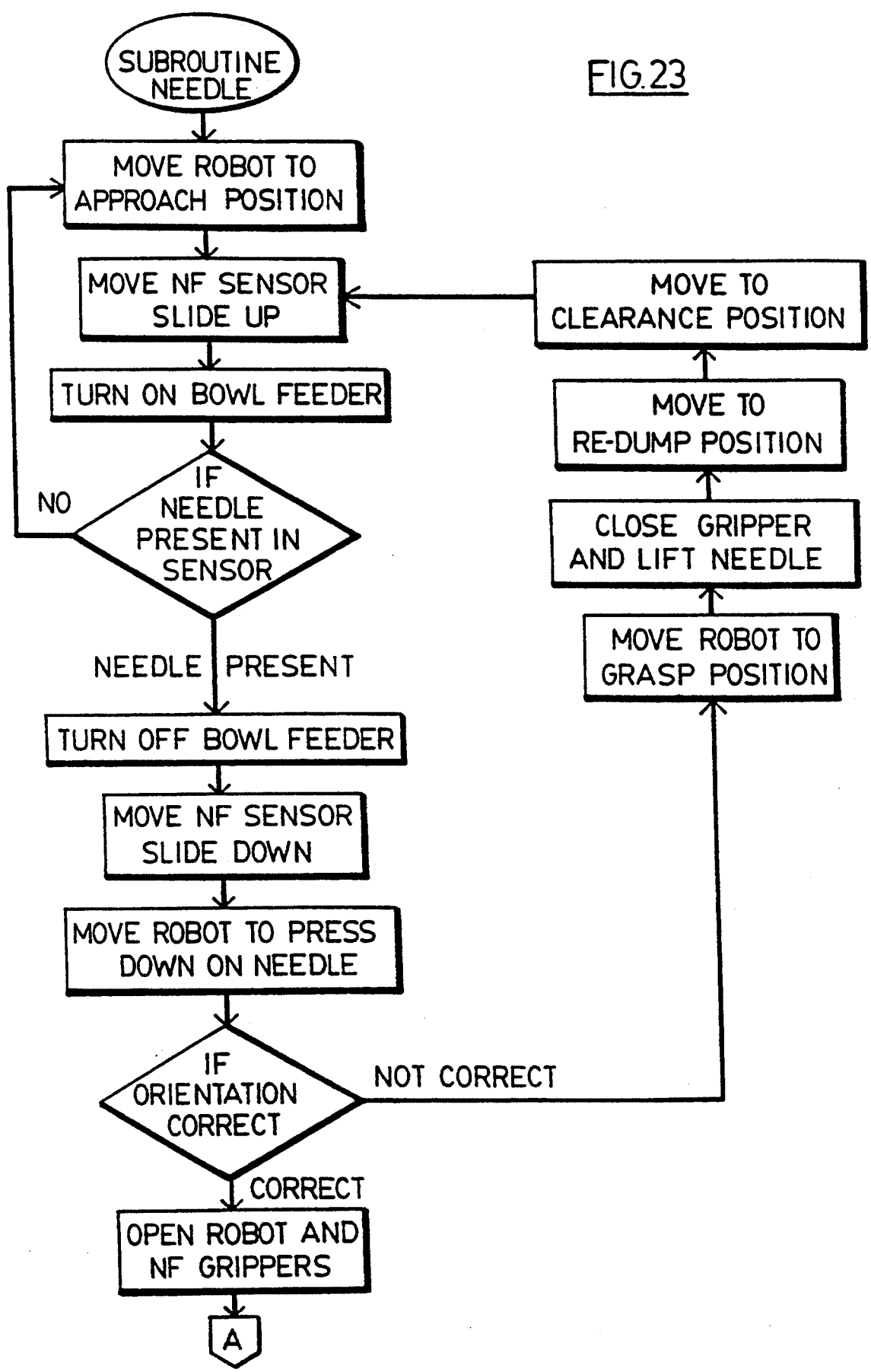
FIG. 23 is a flow chart of sub-routine needle, referred to in FIG. 18.
Figure 23A:
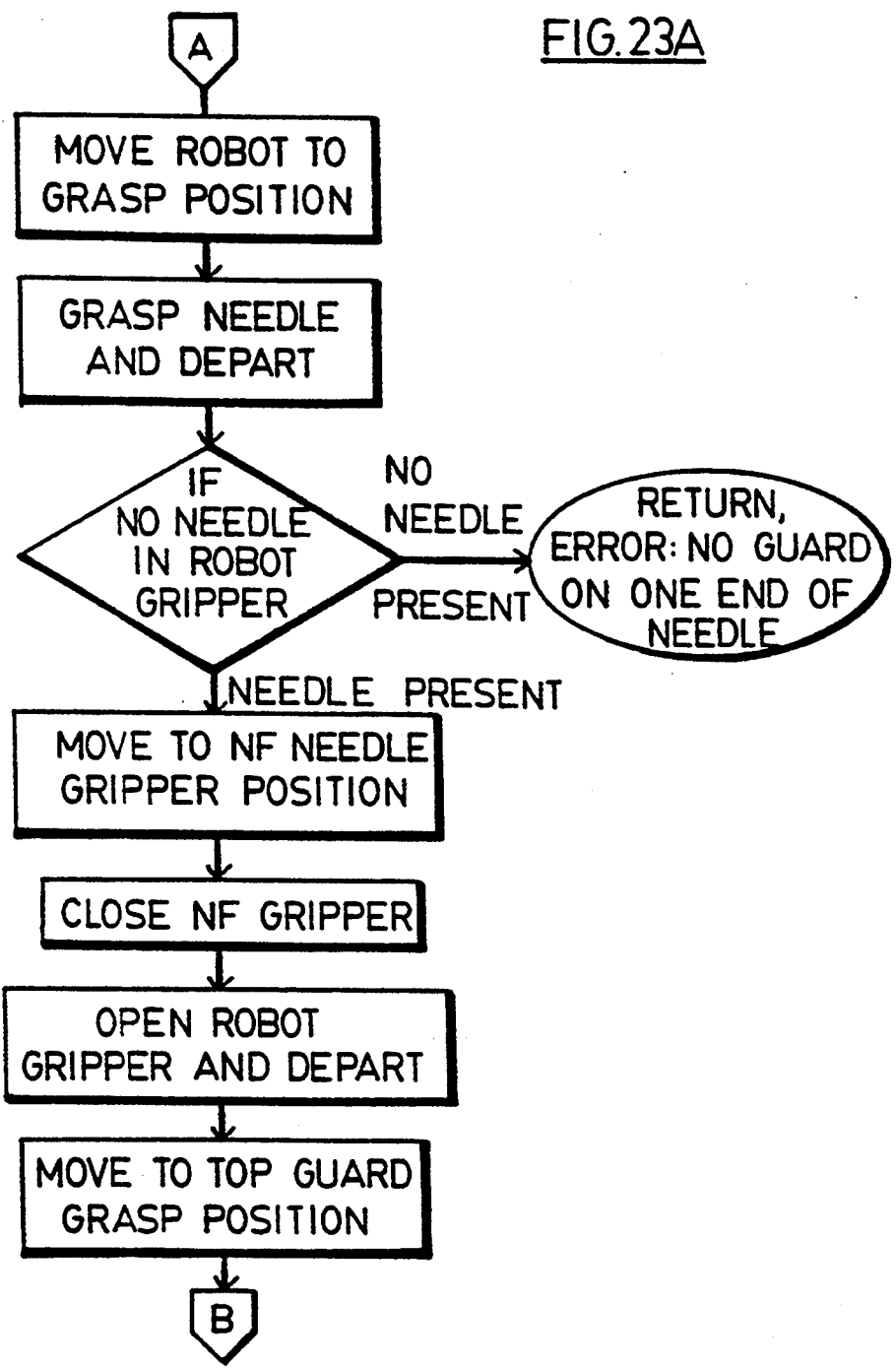
FIG. 23A is a continuation of FIG. 23.
Figure 23B:
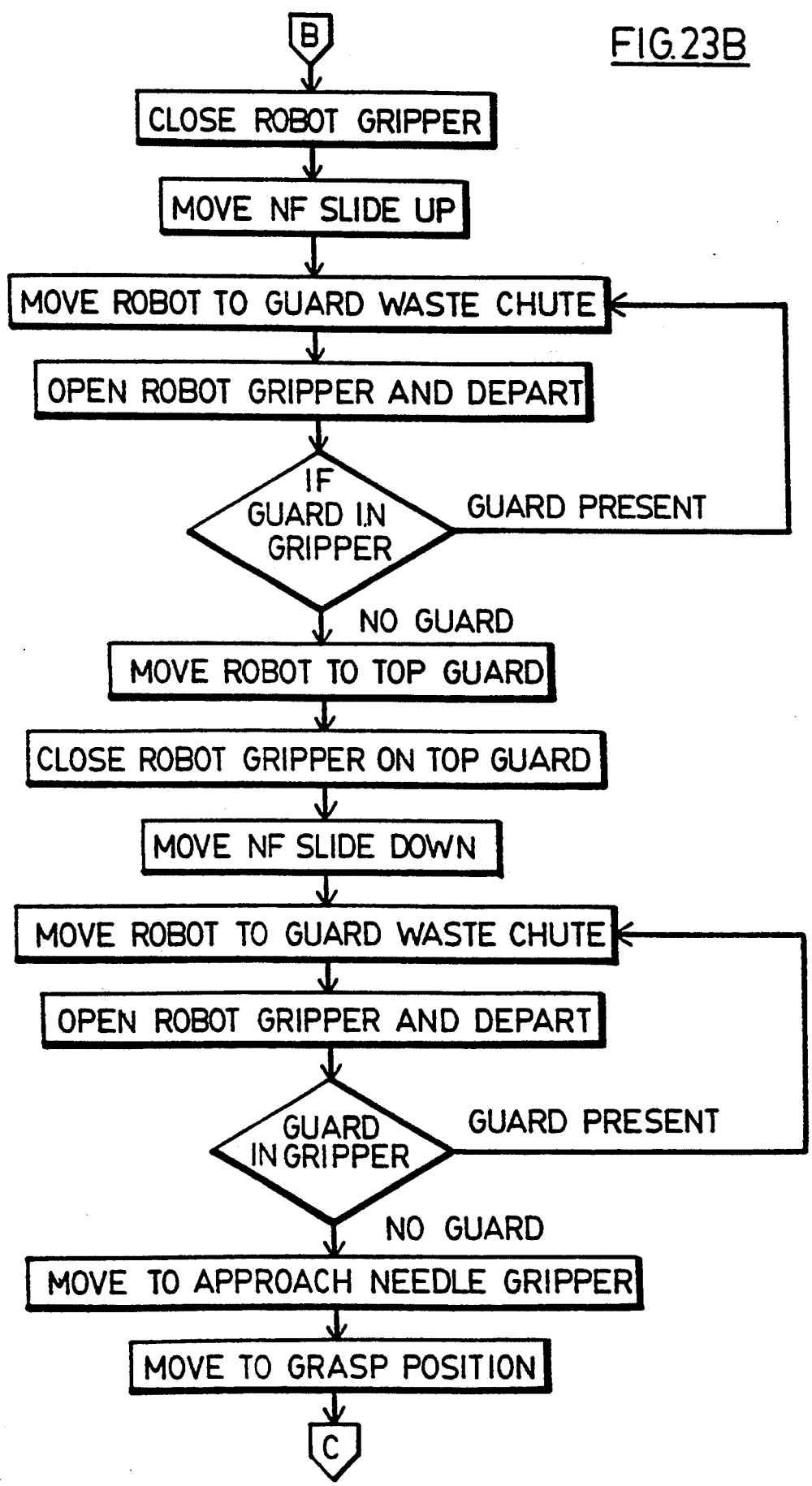
FIG. 23B is a continuation of FIG. 23.
Figure 23C:
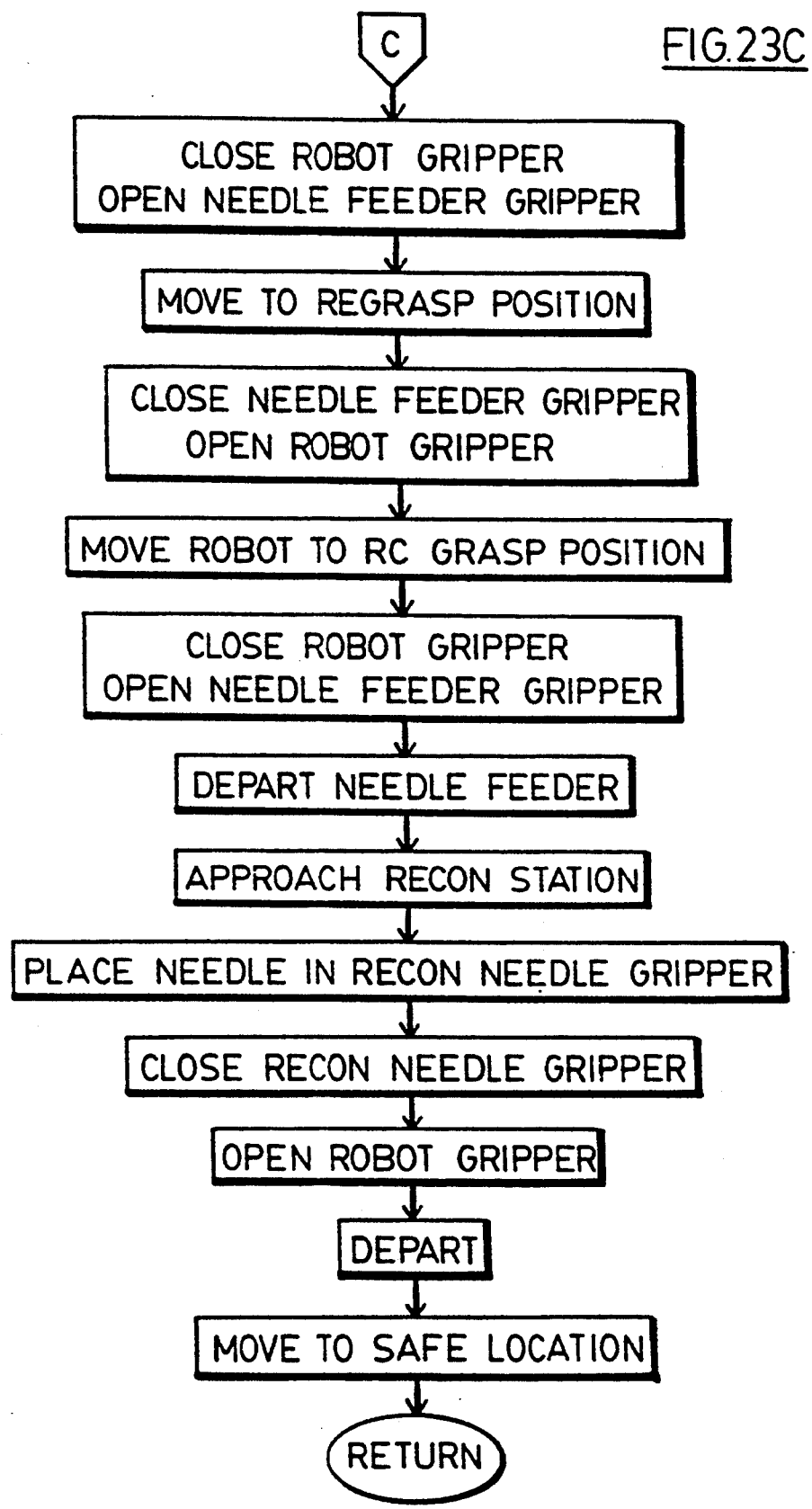
FIG. 23C is a continuation of FIG. 23.
Figure 24:
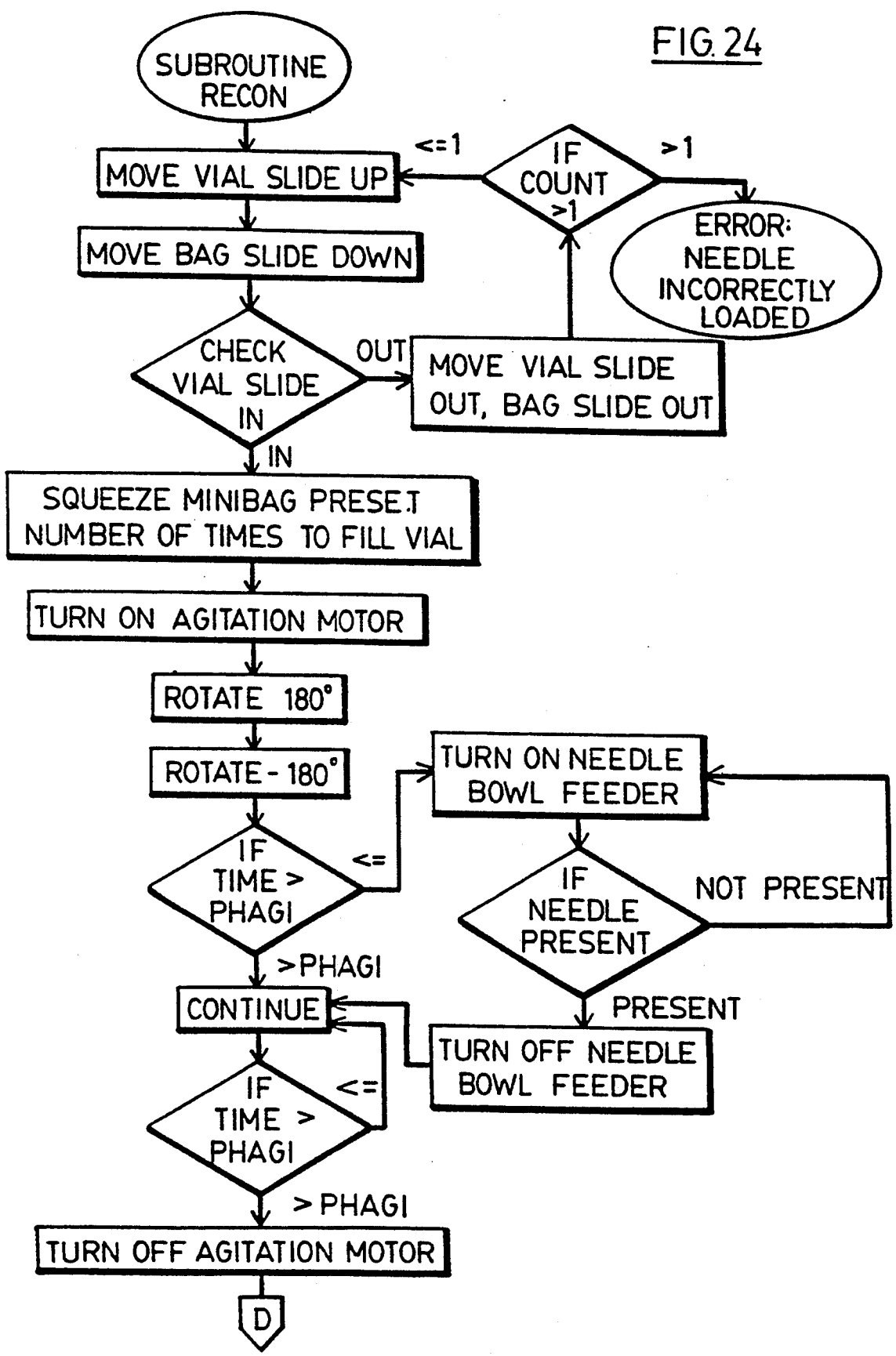
FIG. 24 is a flow chart of sub-routine recon, referred to in FIG. 18.
Figure 24A:
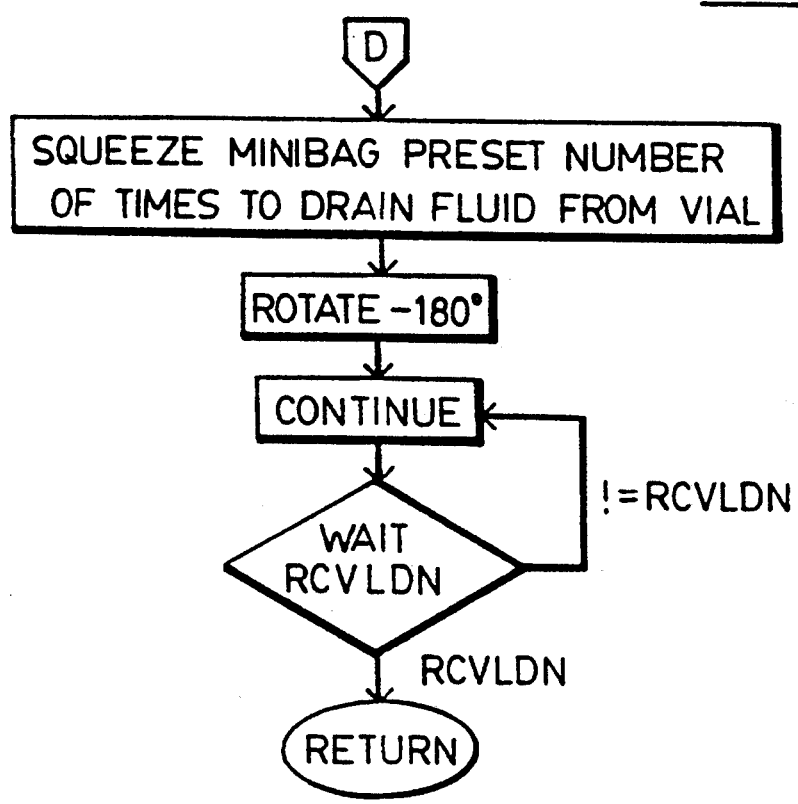
FIG. 24A is a continuation of FIG. 24.

2) This alternative is depicted in detail by the flow chart of FIG. 23.

Control of the process device may be from the robot controller, the computer controller, or from within the process device itself, depending on the capability of the robot controller and the computer controller selected. It is not included in the flow chart illustrations of FIGS. 18–25, but may be summarized as follows:

The process device will finish either the fluid transfer or the reconstitution and send a signal to the robot controller that the operation is complete.

The robot will move the gripper fingers to the vial approach frame of the process device.

The robot will move the gripper fingers to the vial grasp frame and then close the gripper fingers.

The robot controller will signal the process device to release the vial by opening the gripper fingers within the processing unit device.

The robot will then move the vial to the vial depart frame and then to the output chute vial dropoff frame.

The gripper fingers will open and the vial will fall down through the chute to the output queuing system.

If the IV bag trays are used, the robot will move the gripper fingers to the process device tray approach frame and then to the tray grasp frame.

The robot controller will signal the process device to release the solenoid lock on the tray which the processing unit will do and signal back when complete.

The robot will remove the tray containing the IV bag to the tray depart frame and then to the output chute tray approach frame.

The robot will move the tray into a release device which will open the tray using the tray lever and the bag will fall into the output chute, down to the output queuing system tray containing the empty drug vial.

Note: the IV bag may not fall on its own and the release device may have to grasp the bag and force it downwards to release it from the tray. The release device will then let go of the IV bag and let if fall into the output chute as before.

The robot will then take the empty tray to the IV bag feeder tray approach frame where it will then place it back into the bag feeder, release it, and signal the bag feeder that it is clear when it has moved away to the depart frame.

The IV bag procedure may be simplified if trays are not present, as illustrated in FIG. 8 and with reference to the processing unit of FIGS. 14 and 15. In this case:

The robot will move its gripper fingers to the processing unit bag approach frame and then to the hole in the tab of the IV bag.

The robot controller will signal the processing unit to release the locking bars holding the ports of the IV bag which the processing unit will do and signal back when complete.

The robot will remove the bag to the depart frame and then to the output chute approach frame.

The robot will move the bag into a release location and the bag will fall into the output chute, down to the output queuing system tray containing the empty drug vial.

The robot will then go to the processing unit needle approach frame, grasp the needle, move it out of the process device needle clip to the depart frame, then to the discard needle frame, open the gripper fingers and let the needle fall down a disposal chute.

Note: the program may be amended to use the same needle over again if the next prescription in the queue is exactly the same as the previous one.

The robot will signal the Control Computer that the prescription is complete. The Control Computer will then signal the label printer to generate a prescription label appropriate to the prescription just manufactured.

Notes

1. The order of loading the process device may be different than described i.e. vial first, needle second, IV bag third.

2. Corrective action based on sensor input has not been described within although it is part of the robot controller program (i.e. no needles left in needle tray).

3. The process may be optimized by directing the robot to begin preparing the next prescription for the process device by swabbing the vial and IV bag while the current prescription is being completed by the process device.

Figure 4:
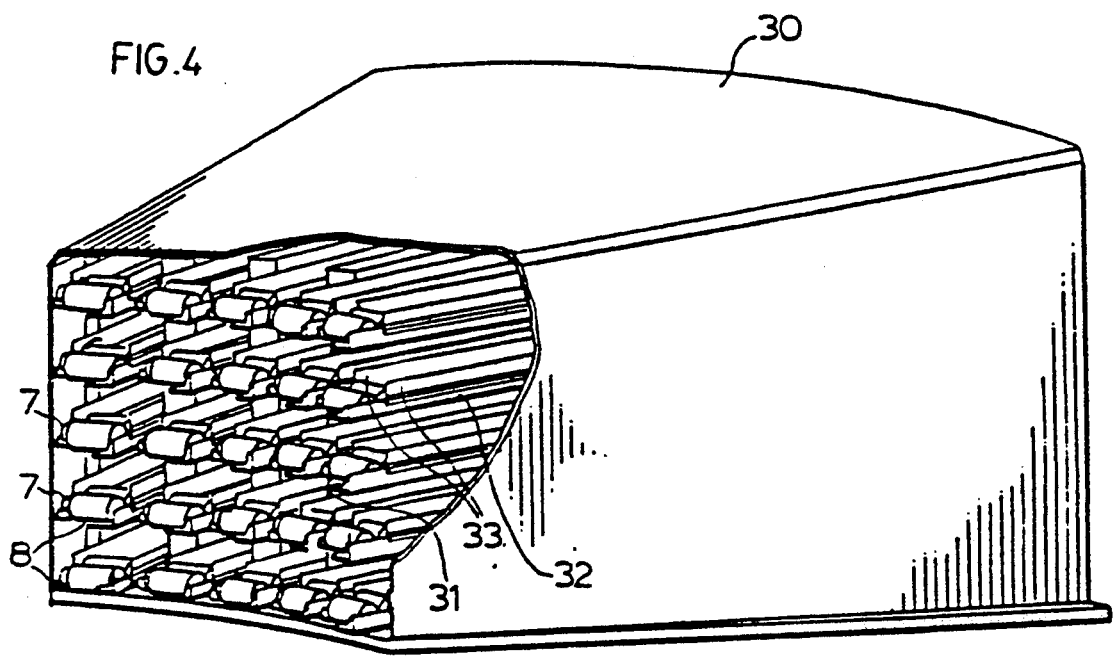
FIG. 4 shows one embodiment of a vial feeder.

The vial dispenser 30 shown in more detail in FIG. 4 may comprise an array of inclined chutes 31, each chute 31 geometrically matched to a particular drug vial geometry to minimize loading errors. A suitable length for each chute may be a suitable length so that it could hold a minimum of twenty-five vials.

Each chute 31 has attached to it a series of tabs 32. These tabs 32 form a binary coded pattern which distinguishes one chute geometry from another and may be sensed by a series of sensors (not shown) in the feed itself. The chutes 31 may be interchangeable so that any chute may be loaded into the array in any position.

The chutes 31 have been designed with guide walls for the ends of the vials 8 such that the robot pick-up location at each chute location remains constant, regardless of the chute type. This means that the location of the top 7 of a drug vial 8 at the end of the chute 31 is related exactly to the robot gripping location. This is done by ensuring the centre axis of the vial is the same for each chute 31. The top 7 of the vial 8 is always towards one wall of the chute 31 and is offset from the chute support rails 33 by a set distance constant for all vials 8. When the robot 20 moves its gripper to any of the vial pick-up locations to pick-up a vial, the center axis of the vial 8 and the vial top 7 are related to the gripper frame by a constant offset which is the same for all vial chutes 31.

The vial dispenser 30 is loaded by placing vials in the chutes 31 from the rear or alternatively, by replacing a chute with a loaded one.

In the drug vial dispenser, each chute is geometrically specific to one vial shape. This means that a larger vial will not fit into the chute of a smaller vial and a small vial will not fit appropriately in the chute of a larger vial. It is felt that once a technician becomes familiar with the loading procedure, the discrepancy of loading a small vial in a larger chute should cause the technician to recognize an error in loading and correct it.

The robot 20 transfers the vial 8 to the decap device 34 which may remove a flip top cap or strip an upper metal tab from the top 7 of vial 8 to expose the diaphragm. The robot 20 then passes the vial 8 to an alcohol swab station 90, if present, and thereafter to the processing unit 60 to be held at its gripper location 65.

One possible IV bag dispenser 40 is shown in FIG. 5 and may be a vertical conveyor upon which individual closed two part trays 42 (see FIGS. 6 and 7) are mounted each of which contains a bag 4. While this description is given with respect to IV bags 4, it is to be understood that syringes might equally well be used. It may be that syringes might be handled directly by robot 20 without the necessity of a tray. The IV bags 4, on the other hand, are flaccid or limp by design and, for handling in an automated system, may be held in a device which can accurately locate the input port 5.

Each bag holding tray 42 is designed to provide sufficient rigidity to the bag and allow the robot to hold the bag tray with the bag in it in any orientation. Suitably the trays 42 may be made of stainless steel, or of plastics material. Loading may be easily and quickly accomplished by simply placing the bag into the open tray 42.

Each tray 42 has two halves hinged together which enclose the bag 4. A lever 43 on one half may be used to open the tray for manual loading with a bag at a loading location A on the dispenser. It is also used to open the tray to take the bag out after processing. Each tray 42 may contain an IV bag 4 of a variety of volumes of liquid. Thus a run of trays may contain IV bags containing one volume for a series of dispensings of one prescription and another run may contain a different volume. The IV bags 4 may be of different sizes or the bags may be of the same size but contain different volumes.

Each tray 42 mounts onto a locating device slat 44 suitably formed, carried on a belt 45 of conveyor 40. These slats 44 have locating keys 46A which hold the trays 42 in position by fitting into a corresponding set of keyholes 46. The robot removes the tray from the slat by moving the tray across the slat to the wider part of the keyhole. There may be guides to prevent the bag tray from disengaging from the slat except at the unloading position.

The conveyor 40 itself consists of a belt 45 which links together slats 44. It has one passive roller 49a a at the top, a drive roller 48 at the front or robot side B, and a roller 49b at the back or loading side of the conveyor. Conveyor tension may be adjusted by altering the angle of the hinged tension roller 47 via a threaded adjustment mechanism. The system may suitably be powered by a suitable motor. The conveyor 40 may have any suitable configuration but is conveniently shown of generally rectangular form. To allow the conveyor 40 to be of a convenient size to carry a suitable number of trays 42, it may be set and located in an inset 41 in the floor of the enclosure.

A control circuit for the conveyor may suitably comprise an operator key switch (load/run), a foot pedal to advance the unit one tray, a pushbutton for reversing the tray direction (in case of loading error), two relays, a position sensing microswitch, an IV bag detection switch (to detect an empty tray), and the cell controller interface hardware and software.

The IV bag dispenser may be loaded from the rear. The technician advances the feeder one position such that another tray moves to the loading position. At this location the tray automatically opens by the lever on the tray contacting a roller connected to a solenoid mounted on the frame. The technician places a bag in the tray with the input port 5 in the split tube support 400 therefore. The operator then advances the feeder to the next position by the use of a foot switch and loads the next bag 4.

Another preferred IV bag dispenser is shown in FIG. 8. In this case the dispenser 40 comprises a combination of a row of IV bags 4 loaded on an elongate hook 502 by means of apertures 504 in the bag. Such apertures 504 are normally provided on the IV bags so that they may be hung on a stand when in use administering fluid to a patient. IV bags 4 in the row are separated by flaps 508 connected to a conveyor belt 510 which belt advances in response to commands from the control computer of the robot controller to advance in steps. For each forward step an IV bag 4 is advanced to be released from hook 502 to be hooked on to one of the gripper arms 200 of the robot 20. In practice, the robot 20 approaches the IV bag dispenser 40 turned so that gripper arm 200A is above gripper arm 200B. Electrical sensor 206 (shown in FIG. 17) senses the presence of hole 504 in tab 506 and gripper arm 202 is inserted hookwise into hole 504. A signal is then sent to the conveyor belt 510 to advance one step and the appropriate flap 508 pushes the IV bag 4 forward of it to be released from hook 502. Robot 20 then moves the bag to the processing unit.

Figure 10:
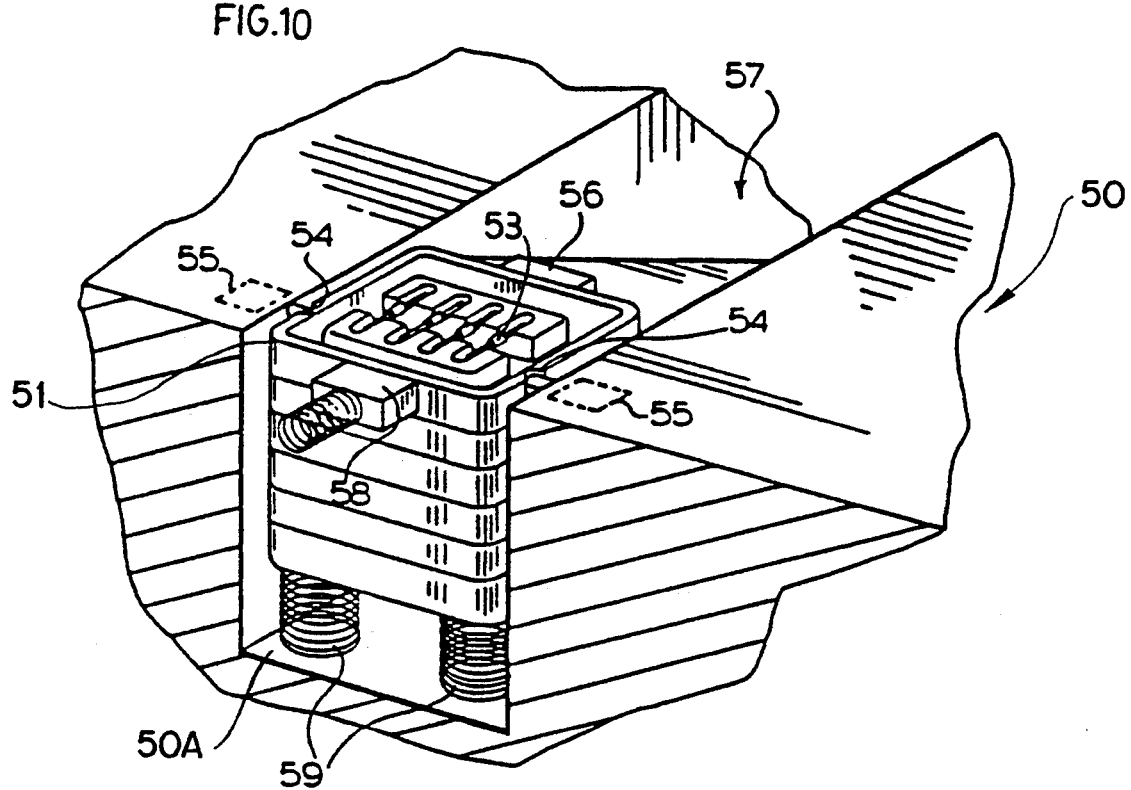
FIG. 10 shows an embodiment of a needle tray feeder.
Figure 11:
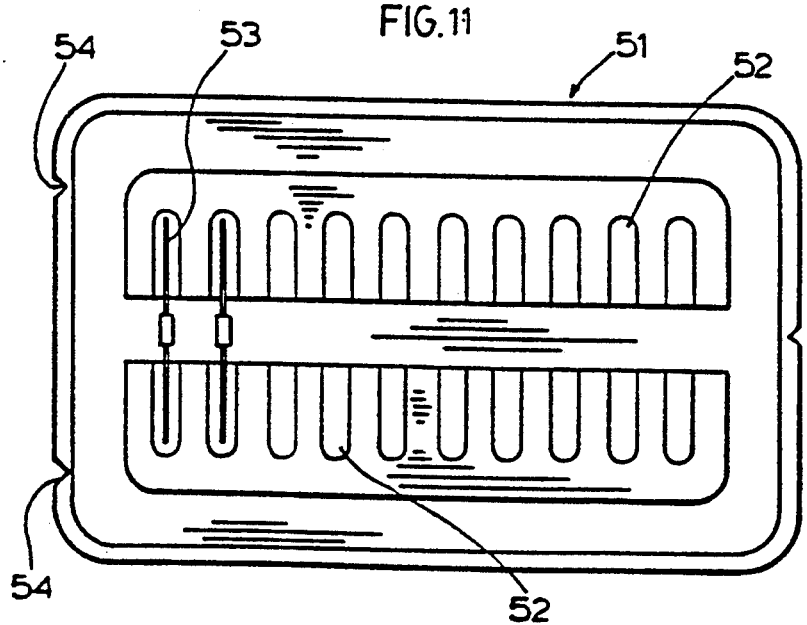
FIG. 11 shows an embodiment of a needle tray.

One form of needle dispenser 50 is as illustrated in FIGS. 10 and 11. The needle dispenser 50 may comprise a well 50A in the floor of the enclosure 10 in which are located needle containing trays 51 containing double ended needles 53. The trays 51 may hold a series of needles (20–40 needles) side-by-side in horizontal troughs 52. The axes of the needles will be parallel. The tray may hold the needles 53 in such a way that a center plastic portion of each needle will be exactly related to the center axis of the needle tray 51. Thus, when the tray is positioned accurately the robot controller knows exactly where the needles are and can move the robot gripper to a point where it can approach, grasp and remove a needle 53 from the tray 51.

Notches 54 in the sides of the tray 51 are provided such that the tray 51 can be located by means of locating clamp pins 55 corresponding to the locating notches 54. A locating clamp plunger 56 to the rear of the tray 51 stops it moving rearwardly under bias from front biassing means 58. The effect of clamping pins 55, plunger 56 and biassing means 58 is to retain the tray 51 accurately in position for removal of needles 53 therefrom.

The tray 51 may be covered with a plastic cover such that the tray of needles can be gas sterilized prior to shipment. This plastic seal is easily removable when the needle tray is in the clamped position, ready to have the robot 20 remove needles 53. For example, a portion of this plastic seal may be peeled back to expose the needles 53. The plastic cover will then be discarded. The robot 20 may reach into the tray and sequentially remove needles from one end to the other and insert them into the processing device. Once the tray is empty of needles, the locating clamp plunger 56 at the rear of the tray may be retracted into the table and the biassing means 58 in the front of the tray will push the tray backwards into a waste chute 57. The tray immediately below the tray that is being removed is held down by two plungers to prevent it from coming up. Once the piston which has pushed the tray out of the way has fully retracted to a clearance position, the plungers that are holding the tray below from coming up may be retracted so that the next tray in line will rise up into the ready position under the influence of biasing means 59. It may then be located and clamped with clamp pins 55 in notches 54 and with plunger 56 and biassing means 58 as described for the previous tray. Stop pins that prevent the tray from rising beyond limits may be provided. Moreover, springs may be provided to bias the stacked trays 51 upwardly. These springs may be such that the force they exert is progressively weaker as the weight of the stacked trays decreases.

Figure 12:
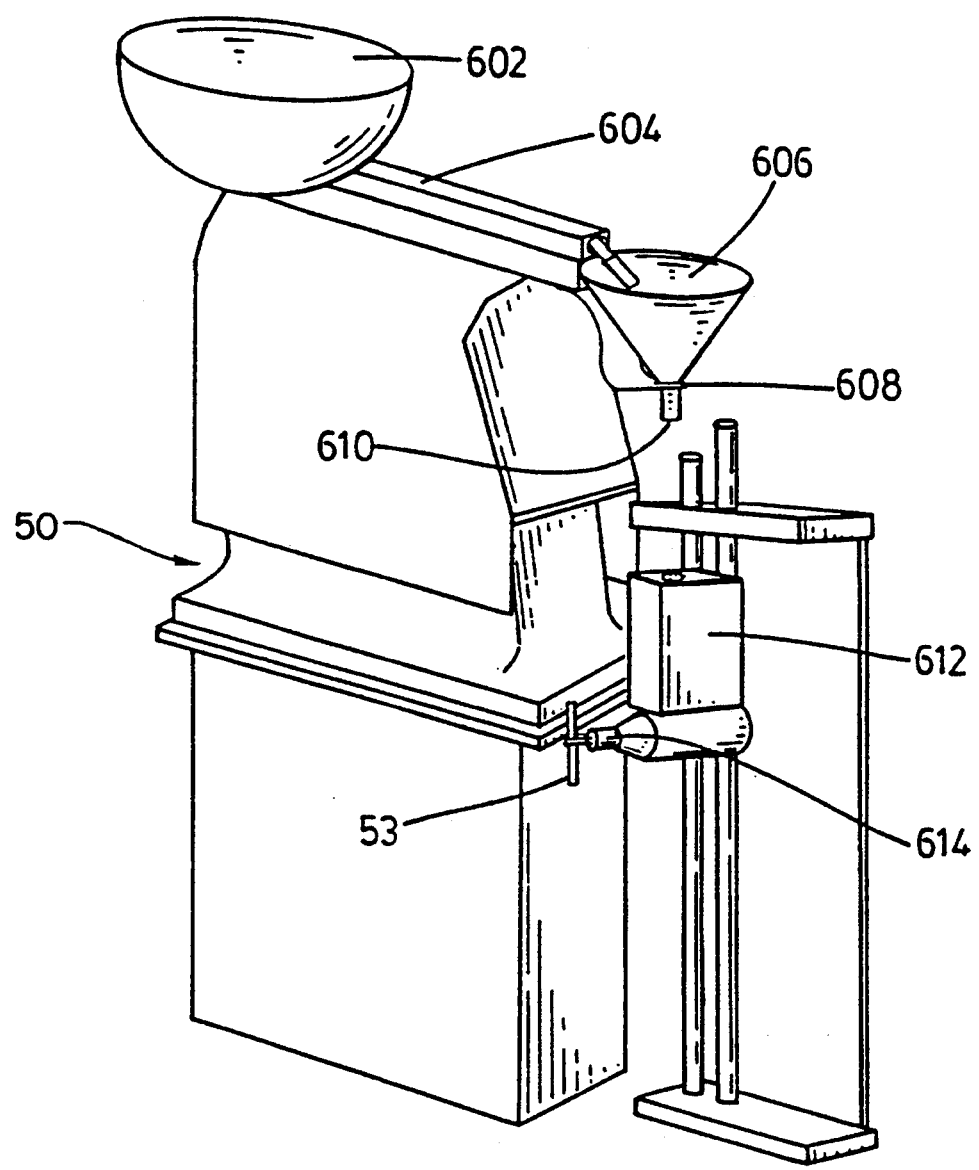
FIG. 12 shows an embodiment of a more preferred needle feeder.

FIG. 12 shows another form of needle dispenser, namely a vibratory bowl feeder which is useful for double-ended hollow needles 53, which may have one end shorter than the other. The needles 53 may be fed from a bowl 602 along a chute 604. The chute 604 dispenses needles to a funnel 606 in which they are oriented end to end. A gate 608 at the downstream end 610 of funnel 606 allows individual needles into a tube 612. Once the needle is in the tube, a blast of compressed air may force the needle to the needle pick-up location 614. This technique is of advantage as it allows the remote location of the dispenser outside the enclosure 10, although, as shown, the arrangement is wholly within the enclosure 10. For this type of needle feeder, only the needle pick-up location 614 need be within the enclosure. The needle dispenser may comprise a gripping bracket to hold a needle 53 at a point between its ends. Needles 53 supplied in this way are sheathed at each end for sterility. Once the needle 53 is gripped at the needle pick-up location 614, the gripper arms may sequentially remove and dispose of the sheaths from each end and then, grip the needle for transport to the processing unit.

Figure 9:
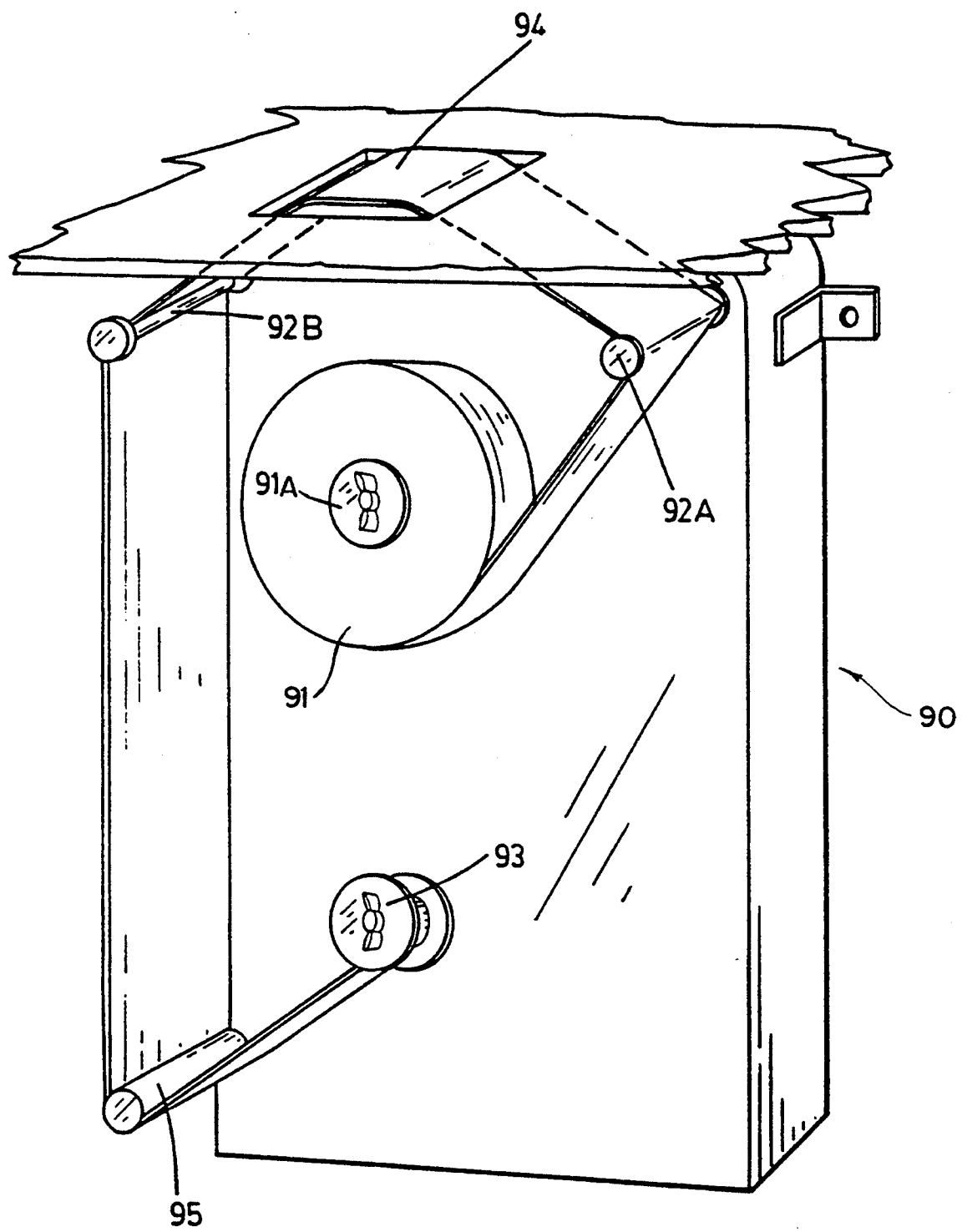
FIG. 9 shows an embodiment of the alcohol swab station.

An alcohol swab station 90 shown in FIG. 9, may be present to swab the input port of each IV bag or syringe, or the top of each vial with an alcohol soaked section of gauze for sterilization purposes. Current manual techniques involve swabbing the top of the drug vial and the input port of the IV bag with an alcohol soaked piece of gauze.

The alcohol swab station 90 comprises a roll 91 of sterile gauze, e.g. four ply sterile gauze, threaded through a series of rollers to a takeup reel 93. At the front center of the station, the gauze passes over a flat moveable swabbing surface 94 with a small orifice (not shown). Through this orifice alcohol is pumped to soak a section of gauze. The robot presses the vial top and/or the input port of the IV bag against this section of soaked gauze and wipes it up, possibly repeatedly. This effects similar swabbing action as is currently carried Out by the technician in the present conventional manual technique.

The operator loads this station by placing the gauze roll 91 on the front spool 91A, threading the gauze past the first guide roller 92A, past the moveable swabbing surface 94, past second guide roller 92B, around an encoding roller 95, and onto a removal blank on the takeup reel 93. A manual switch is depressed, turning the takeup reel motor on to ensure the gauze is being fed properly. The swabbing surface may be mounted with positioning rods and springs to allow the swabbing surface to wipe the appropriate surface presented to it. The tension of the springs may be adjusted manually.

The takeup reel 93 may be driven by a small electric motor. The distance moved by the gauze is measured on the encoding roller 95. A resolution for this encoder may be within $\frac{1}{8}$ inch travel.

The processing unit 60 shown in FIG. 13 may comprise two short stroke pneumatic slides 61, 62 which move the drug vial 8 up and the IV bag tray 42 down. The slides may, for example, be pneumatically operated but other manners of operation are possible. A 180° pneumatic rotation module 63 is provided to support the two slides 61, 62 and a needle holder 64. A pneumatic gripper 65 holds the drug vial 8 by the collar and a small electric motor is provided to agitate the drug vial 8. A low pressure pneumatic cylinder is provided to provide squeezing force on the IV bag. In addition there are various pneumatic and electric control components.

The robot places a needle 53 into the gripper 64 which holds it by the cylinders on either end of the centre robot grip point, i.e. immediately above and below the robot gripper location. The gripper 64 may be, for example, a pneumatically operated clip or a spring clip or other gripper should not only hold the needle axis vertical but also prevent it from moving up or down.

The robot places a drug vial 8 into the processing unit, at a point where a gripper 65 of the processing device grasps it by the collar. The gripper 65 may be bevelled to center the cap and prevent it from moving. The gripper 65 is mounted in the bushing 66 and can rotate in the horizontal axis perpendicular to the needle/vial axis. This bushing is mounted on the pneumatic slide 61 which is at its lowermost position during loading.

The robot 20 may place a loaded IV bag tray 42 into the fixture with the input port 5 of the IV bag 4, which is inside the split tube support 400 pointing downwards. The tray 42 is held by locating keys such as those on the IV bag feeder slats 44 in the key holes 46 and is held from moving by a plunger (not shown on the drawings). The holding bracket is mounted on a short stroke pneumatic slide 62 which is at its uppermost position during loading.

The above components may be positioned such that the input ports of the IV bag inside the split tube support 400, the needle, and the centre of the drug vial cap are aligned along the axis of the needle. Once loaded, the robot 20 signals its controller that it has moved away and then the pneumatic slides 61, 62 activate, forcing the needle 53 to puncture both the top 7 of the drug vial 8 and the input ports 5 of the IV bags 4. A fluid connection between the two is established. It should be noted that the stroke length of these slides 61, 62 can be adjusted so that the needle penetration into the vial and bag may be adjusted to desired depths. It may be an advantage if the top of the vial is contoured slightly to guide the needle tip to puncture it centrally. This may be achieved by a center dip in the vial top.

The processing unit of FIG. 14 differs from that of FIG. 13 in that it is designed for use with IV bags without trays. FIG. 14 shows a processing unit 60 having a hook 702 on a vertical plate 704. The robot 20, shown in FIG. 8 transfers the IV bag 4 onto hook 702 by approaching the hook so that the hole 504 in tab 506 moves over hook 702. The robot 20 then withdraws its gripper arms 200. The IV bag 4 hangs freely on hook 702 until the processing unit is actuated by a signal to close a locking bar 706. The bar 706 moves in one horizontal direction at right angles to the plane of the IV bag containing its ports, to lie against the ports 5, 5A to bias them against a corresponding bar 707 or against the plate 704. Bar 706 may have a profiled inner surface to accommodate the IV bag ports 5, 5A without squashing them. While holding them in position, a second locking bar 708 is actuated in a horizontal direction at right angles to that of bar 706 to bear against it. It acts against a corresponding stop plate 709 so that the ports 5, 5A of the IV bag are securely locked against lateral movement, and also holds them against vertical movement. The operation of puncturing the drug vial 8 and the input port 5 of the IV bag 4 are as described for the processing unit of FIG. 13.

The reconstitution process in the processing unit 60 is similar for both the apparatus of FIG. 13 and FIG. 14.

To the side of the IV bag tray 42 (FIG. 13) or un-trayed IV bag 4 (FIG. 14), is a short-stroke pneumatic piston 67 which has a large diameter plunger mounted on it. This piston is connected to a pressure reducer. The piston is activated, forcing the plunger (through a corresponding hole in the tray for FIG. 13), to squeeze the IV bag. When a tray is present its other side is supported by a bracket. The pressure exerted is reduced to a point where the IV bag can safely handle the external squeezing pressure. A flow regulator may also be needed to prevent the piston from squeezing too fast.

The piston 67 and plunger cyclically activate, performing a pumping action on the IV bag 4. This forces fluid down through the needle 53 into the drug vial 8. This continues for a preset number of cycles until the drug vial 8 is nearly full of fluid. The number of cycles will depend on the mixing requirement of the specific drug, and size of the vial currently in the fixture and is stored in the controller database.

The vial 8 is now full of fluid and powder. A small electric motor 68 is mounted on the same bracket that holds the bushing 66 support which in turn holds the gripper 65. The motor 68 is turned on by the controller. Its shaft is eccentrically cam mounted to a lever which is attached to the gripper 65. This results in the oscillation of the drug vial about the shaft axis. The magnitude of oscillation may be only a few degrees but will be sufficient to cause high turbulence in the fluid within the drug vial 8. This turbulence causes the powder to dissolve into the liquid. This continues for a computer determined length of time, appropriate for the drug, vial size, amount of drug contained in the vial, and the solubility characteristics.

Both pneumatic slides 61, 62 and the needle holder 64 are mounted by way of a bracket onto a pneumatic rotation module 63. This module is then activated, rotating the bracket and components 180° about the horizontal axis (parallel to the gripper shaft). This situation may be seen in FIG. 15 which shows the inverted condition of the processing unit of FIG. 14. The drug vial 8 is now held upside down above the needle 53 and the IV bag 4.

The IV bag piston 67 and plunger are again cyclically activated, forcing the gas in the IV bag 4 into the vial 8 and, when pressure is released by the piston, fluid back into the IV bag 4. This action continues for a computer determined number of cycles stored in the computer controller database until all possible fluid is returned to the IV bag 4. The pneumatic slides 61, 62 are then activated separating the needle 53 from both the IV bag 4 and the drug vial 8.

This station can also be used to transfer fluid from a unit dose vial into the IV bag by simply skipping the initial fluid transfer into the vial and the vial agitation steps.

When an IV bag tray 42 is present (FIG. 13), the robot 20 removes the IV bag tray 42 and drug vial 8 and unloads them into the output 70. When no tray is present, the processing unit releases locking bars 706 and 708 in the inverted position, thus allowing bag 4 to fall off hook 702 into output 80. The output 70 comprises a chute having the loading location within the filtered enclosure 10. The empty drug vial 8 and the bag fall through the chute into trays 71 the bases of which may be narrower than the mouth. The base should be wider than the width of the largest drug vial under consideration. Each of these trays 71 fits into a slot 73 (not shown) between wedges of a conveyor. The conveyor may be a belt 74 having its plane vertical and the path of travel being a loop in the horizontal plane. The wedges 72 may be attached to the plane of the belt 74. The belt 74 may be contained in an outside rail as well as an inside rail. The drive mechanism may be an electric motor and encoders may be provided to position the tray to receive the IV bag and the empty drug vial. The system may be capable of holding at least 20 prescriptions (which constitute an IV mini bag with a drug solution in it as well as the empty drug vial). The technician can remove each one of these trays from the conveyor to remove its contents to an examination area for manual verification of the prescription. The trays may be sterilized when removed.

The system may be capable of holding a minimum of 20 prescriptions. The technician may advance the conveyor by depressing a foot pedal switch or by a manual push button switch either of which must be depressed for activation. The technician can then advance to a new section of the conveyor and unload between 5 and 10 trays at once, maintaining the correspondence between prescriptions and the empty vials. The robot removes the needle 53 from the clip 64 and delivers it to a discard location 9.

A label printer 75 may be provided and may be any suitable conventional label printer to receive and print data for the label according to prescription data. The robot 20 may be additionally programmed to pick-up a label from the printer and deliver it to the output 70 with the respective IV bag 4 and vial 8.

At the operator area 40 which is the delivery location of output 70, the operator will have the empty drug vial, the IV bag and possibly also a label with the prescription order. This must be checked against the original prescription. The technician shall read through the original prescription and compare it with the components and the generated label. If satisfactory, the label could be applied to the IV bag to reduce the risk of administration errors (i.e. wrong patient, wrong start time, etc.). Alternatively, if bar codes exist on the components and the label itself, the technician could simply use an optical wand to check the accuracy of the label with the prescription received and then use the same wand to check the components against the prescription components required. This would be simplified if the prescription is received electronically from the hospital main computer.

Sterile enclosure 10 may comprise a support structure for a flow hood such as a HEPA filtered ventilation hood. The structure 11 may suitably be a tubular steel form.

To reduce contamination risk during loading, the technician may use sterile gloves and wear a mask. A panel section on the robotic area enclosure is raised and the technician performs loading operations within the filtered air environment. The vials, needles, IV bags and gauze may all be supplied in containers which themselves should maintain the sterility of the contents. These containers are opened within the filtered air enclosure and components are then loaded. At no time do the needle insertion surfaces come in contact with any other surface.

The relevant components of the fixtures in the cell are easy to sterilize. Each drug vial chute is removable as are the IV bag trays. These could be sterilized in a bath if so required. The reconstitution station can have the vial and needle holders easily cleaned by a technician. Each output tray can be removed from the carousel and sterilized. It should not be necessary to sterilize the alcohol swab station or the needle feeder.

INDUSTRIAL APPLICABILITY

The invention may be applicable to dispensing systems for pharmaceuticals into containers such as IV bags. It may also be applicable to

What is claimed is:

1. An automated robotic dispensing system for introducing a unit drug dose from a vial having a top diaphragm pierceable by a needle into a container of solute therefor, comprising:
   a filling station enclosed in a filtered environment, the filling station comprising a manipulating robot, a vial dispenser, a container dispenser, at least a needle pick-up location of a needle dispenser, a processing unit, a loading location of an output for processed containers, and a discard location; the robot being programmed to:
   (a) receive a said vial containing a said unit drug dose from a vial pick-up location of the vial dispenser and deliver it to a vial reception location of the processing unit;
   (b) receive a said container from the container dispenser at a container pick-up location and deliver the container to a container reception location of the processing unit;
   (c) receive a said needle from the needle dispenser at the needle pick-up location and deliver the needle to a needle holder of the processing unit;
   (d) receive the processed container from the processing unit and deliver it to the output;
   (e) receive the empty vial from the processing unit and deliver it to the output; and
   (f) receive the used needle from the processing unit and discard it to a discard location;
   the vial dispenser being adapted to hold a plurality of vials each containing a said drug dose and to deliver them sequentially to the vial pick-up location;
   the container dispenser being adapted to hold a plurality of containers each container containing solute for the drug dose and to deliver them sequentially to the container pick-up location;
   the needle dispenser being adapted to hold a plurality of double-ended needles and to deliver them sequentially to the needle pick-up location;
   the processing unit including means for moving a said vial, a said needle and a said corresponding container into fluid communication through the needle, and means for flowing fluid from the container to the vial and vice-versa to dissolve the unit drug dose and transfer the solution to the container.

2. An automated robotic dispensing system as claimed in claim 1, in which the containers are IV bags.

3. An automated robot dispensing system as claimed in claim 2, in which the output comprises a chute having the loading location within the filtered environment and a discharge location outside it.

4. An automated robotic dispensing system as claimed in claim 2, in which the vial pick-up location is one of a set of vial pick-up locations.

5. An automated robotic dispensing system as claimed in claim 2, in which the container dispenser comprises an elongate hook adapted to releasably hold a row of IV bags, separated by stepping advance means secured to an endless belt conveyor, whereby each bag is advanced one step on each stepped advance of the conveyor.

6. An automated robotic dispensing system as claimed in claim 5, in which the processing unit includes needle gripping means for the needle adapted to hold it vertical; vial gripping means for a said vial adapted to locate the vial such that the diaphragm vial top is located to be pierced by the needle on closing movement between the needle and the vial; and tray gripping means for an IV bag tray adapted to locate the tray such that an input port of the bag is located to be pierced by the needle on closing movement between the need and the tray.

7. An automatic robotic dispensing system a claimed in claim 6, in which:
   first slide means are provided to move the vial gripping means and hence the vial vertically upwardly towards the needle by an amount at least sufficient for the needle to pierce the diaphragm vial top; and
   second slide means are provided to move the tray gripping means and hence the bag vertically downwardly towards the needle by an amount at least sufficient for the needle to pierce the input port seal(s) of the container.

8. An automatic robotic dispensing system as claimed in claim 7, in which means are provided to agitate the vial by rotation of the vial about an acute angle whose apex is substantially at a needle insertion point.

9. An automated robotic dispensing system as claimed in claim 7, in which:
   the vial gripping means, the needle gripping means and the tray gripping means are rotatable as a unit between a first position in which they are vertically located one above another with the vial gripping means being lowermost; and
   a second position in which they are vertically located one above another with the tray gripping means being lowermost.

10. An automated dispensing system as claimed in claim 5, in which the processing unit includes needle gripping means for the needle adapted to hold it vertical; vial gripping means for the vial adapted to locate the vial such that the diaphragm vial top is located to be pierced by the needle on closing movement between the needle and the vial; the hook for the IV bag to locate it such that an input port of the bag is in a location to be pierced by the needle in closing movement between the needle and the bag; and means to clamp the input port in said location.

11. An automated dispensing system as claimed in claim 10, in which the clamping means comprises a first pair of clamping bars adapted to hold the input port therebetween.

12. An automated dispensing system as claimed in claim 11, in which an additional pair of clamping bars is provided acting at right angles to the first pair of clamping bars to stabilize the position of the bag.

13. An automated robotic dispensing system as claimed in claim 10, in which:
first slide means are provided to move the vial gripping means and hence the vial vertically upwardly towards the needle by an amount at least sufficient for the needle to pierce the diaphragm vial top; and
second slide means are provided to move the IV bag vertically downwardly towards the needle by an amount at least sufficient for the needle to pierce the input port seal of the container.

14. An automated robotic dispensing system as claimed in claim 10, in which means are provided to agitate the vial by rotation of the vial about an acute angle whose apex is substantially at the needle insertion point.

15. An automated robotic dispensing system as claimed in claim 10, in which:
the vial gripping means, the needle gripping means and the hook are rotatable as a unit between a first position in which they are vertically located one above another with the vial gripping means being lowermost; and
a second position in which they are vertically located one above another with the hook being lowermost and the bag being supported by the clamping means.

16. An automated robotic system as claimed in claim 1, including an alcohol swabbing station for the vials and containers.

17. An automated robotic dispensing system as claimed in claim 16, in which the alcohol swabbing station comprises an absorbent swabbing web at a swab location, and means to impregnate the web with alcohol at the swab location; the robot being additionally programmed to contact the top diaphragm of the vial and/or an input port of the container with the web at said location before delivery of the vial and/or the container to the processing unit; and stepping means to advance the web a step after each contact of the diaphragm or input port.

18. An automated robotic dispensing system as claimed in claim 1, in which the vials are initially capped over the diaphragm top and the robot is adapted to uncap each vial.

19. An automated robotic dispensing system as claimed in claim 1, which includes a label printing device and in which the robot is additionally programmed to receive a label from the labelling device and deliver it to the chute.

20. An automated robotic dispensing system as claimed in claim 1, in which the vial dispenser comprises at least one inclined chute having the vial pick-up location, the chute being adapted to receive a specifically sized vial.

21. An automated robotic dispensing system as claimed in claim 20, in which the vial fits between walls of the chute.

22. An automated robotic dispensing system as claimed in claim 20, in which the vial dispenser comprises more than one inclined chute, different ones of which are adapted for different sizes of vials.

23. An automated robotic dispensing system as claimed in claim 22, in which the robot is programmed to select a said vial from the pick-up location of a particular chute according to prescription data.

24. An automated robotic dispensing system as claimed in claim 1, in which the container dispenser comprises a conveyor in combination with trays, the conveyor comprising a belt of interlinked slats, and each tray being adapted to contain the IV bag and being hingeably connectable to the slat of the conveyor at an edge of the tray.

25. An automated robotic dispensing system as claimed in claim 1, in which the needle dispenser comprises stacked needle containing trays located in a well of a floor of the filling station, first biasing means adapted to bias the stacked trays upwardly whereby the top tray has a location at least at floor level of the filling station; releasable retaining means adapted to retain the top tray in said location for removal of the needles therefrom; second biasing means adapted to bias the top tray towards the discard location; and releasing means adapted to release said retaining means whereby the top tray is moved by said second biassing means to the discard position.

26. An automated robotic dispensing system as claimed in claim 25, in which each needle containing tray is adapted to contain needles arranged one parallel to another for sequential removal by the robot.

27. An automated robotic dispensing system as claimed in claim 26, in which each needle containing tray is adapted to contain needles with end portions thereof located to each side of an axis of the needle containing tray.

28. An automated robotic dispensing system as claimed in claim 27, in which the processing unit includes means for agitating the vial by rotation of the vial about an acute angle whose apex is substantially at a needle insertion point.

29. An automated robotic dispensing system as claimed in claim 28, in which:
first slide means are provided to move the vial gripping means and hence the vial vertically upwardly towards the needle by an amount at least sufficient for the needle to pierce the diaphragm vial top; and
second slide means are provided to move the container gripping means and hence the container vertically downwardly towards the needle by an amount at least sufficient for the needle to pierce the input port seal(s) of the container.

30. An automated robotic dispensing system as claimed in claim 1, in which the needle dispenser comprises a container for loose needles, a chute outlet from the container, a funnel to orientate needles in a selected direction, a dispensing gate for individual oriented needles and gripping means for an oriented needle at the pick-up location.

31. An automated robotic dispensing system as claimed in claim 1, in which the processing unit includes needle gripping means for the needle adapted to hold it vertical; vial gripping means for the vial adapted to locate the vial such that the diaphragm vial top is located to be pierced by the needle on relative vertical movement between the needle and the vial, and container holding means for the container adapted to locate the container such that an input port of the container is located to be pierced by the needle on relative vertical movement between the needle and the container.

32. An automated robotic dispensing system as claimed in claim 1, in which the output comprises the chute having the loading location within the filtered environment and a lower discharge end outside the filtered environment and the output also comprising a receiving tray for each of an IV bag and its respective vial from which it has received a drug dose, and a conveyor adapted to convey each tray from the lower discharge chute end to a delivery location.

33. An automated process for introducing, in a filling station in a filtered environment, a unit drug dose from a vial having a top diaphragm pierceable by a needle into a container of solute therefore, the filling station comprising a manipulating robot, a vial dispenser, a container dispenser, at least a needle pick-up location of a needle dispenser, a processing unit, a loading location of an output for processed containers and a discard location, comprising the steps of:

sequentially delivering a said vial to a pick-up location of the vial dispenser which is adapted to hold a plurality of vials each containing a said unit drug dose;

sequentially delivering a said container to a pick-up location of the container dispenser which is adapted to hold a plurality of containers containing solute for the unit drug dose; and sequentially delivering a said needle to the pick-up location of the needle dispenser which is adapted to hold a plurality of double-ended needles; and the robot receiving a said vial containing a said unit drug dose from the vial pick-up location of the vial dispenser and delivering it to a vial reception location of the processing unit;

the robot receiving a said container from the container dispenser at the container pick-up location and delivering the container of a container reception location of the processing unit;

the robot receiving a said needle from the needle dispenser at the needle pick-up location and delivering the needle to a needle holder of the processing unit;

at the processing unit, moving a said vial, a said needle and a said corresponding container into fluid communication through the needle, and flowing fluid from the container to the vial and vice-versa to dissolve the unit drug dose and transfer the solution to the container;

the robot receiving the processed container from the processing unit and delivering it to the output conveyor;

the robot receiving the empty vial from the processing unit and delivering it to the output; and the robot receiving the used needle from the processing unit and discarding it to a discard location.

34. A process as claimed in claim 33, including the step of programming the robot.

35. A process as claimed in claim 34, in which the robot selects a said vial from a plurality of pick-up locations according to prescription data.

36. A process as claimed in claim 33, including the step of the robot decapping an initially capped vial on reception from the vial pick-up location to uncover the diaphragm.

37. A process as claimed in claim 33, in which the containers are IV bags.

38. A process as claimed in claim 33, in which the filling station is enclosed in the filtered environment.

39. A process as claimed in claim 38, which also includes the step of the robot presenting each of the decapping vial and the container at an alcohol swabbing station and swabbing the diaphragm and an input port of the container with alcohol.

40. A process as claimed in claim 33, including the step of the robot receiving a label from a label printing device and delivering it to the output.

41. A process as claimed in claim 33, which includes, at the processing unit, moving a said vial, a said needle and a said corresponding container into fluid communication through the needle, and transferring the liquid drug solution to the container from the vial.

* * * * *